United States Patent [19]

Faustini et al.

[11] Patent Number: 4,626,597
[45] Date of Patent: Dec. 2, 1986

[54] 16-FLUORO-16,17-DIDEHYDRO PROSTANOIDS AND PROCESS FOR THEIR PREPARATION

[75] Inventors: Franco Faustini, Milan; Roberto d'Alessio, Cinisello Balsamo; Achille Panzeri, Merate; Enrico di Salle, Milan, all of Italy

[73] Assignee: Farmitalia Carlo Erba, S.p.A., Milan, Italy

[21] Appl. No.: 643,014

[22] Filed: Aug. 22, 1984

[30] Foreign Application Priority Data

Sep. 7, 1983 [GB] United Kingdom ............... 8324004

[51] Int. Cl.$^4$ ............................. C07C 177/00
[52] U.S. Cl. ........................ 560/53; 560/121; 562/463; 562/464; 562/465; 562/503; 564/102; 564/169; 564/170; 544/59; 544/172; 544/391; 546/225; 548/248; 548/378; 549/480; 549/505
[58] Field of Search ............... 560/53, 121; 562/463, 562/464, 465, 503; 564/102, 169, 170; 544/59, 172, 391; 546/225; 548/248, 378; 549/480, 505

[56] References Cited

U.S. PATENT DOCUMENTS 3,987,087 10/1976 Bundy .................................. 560/53
4,059,576 11/1977 Holland et al. ...................... 560/53
4,229,585 10/1980 Pellegata et al. .................... 560/53

OTHER PUBLICATIONS

Derwent Abstract No. 61615X.
Derwent Abstract No. 72455W.
Derwent Abstract No. 09124W.
Derwent Abstract No. 69717U.
Derwent Abstract No. 64097D.
Derwent Abstract No. 42013D.
Derwent/Farmdoc 83-807749 (U.S. Pat. No. 4,410,720).
Derwent/Farmdoc 87208D (U.S. Pat. No. 4,298,754).
Derwent/Farmdoc 83776888 (U.S. Pat. No. 4,404,393).
Derwent/Farmdoc 12825A (Japanese patent application No. J50140427).
Chemical Abstract 86-155241d (German No. 2517771).

Primary Examiner—Paul J. Killos
Attorney, Agent, or Firm—Murray and Whisenhunt

[57] ABSTRACT

16-Fluoro-16,17-didehydro prostanoids, processes for their preparation, compositions containing them and methods of using them are disclosed. The compounds and compositions have pharmaceutical utility including, for example, luteolytic activity.

17 Claims, No Drawings

16-FLUORO-16,17-DIDEHYDRO PROSTANOIDS AND PROCESS FOR THEIR PREPARATION

The present invention relates to new 16-fluoro-16,17-didehydro prostanoids, to a process for their preparation, to pharmaceutical and veterinary compositions containing them, and to intermediates useful for their synthesis. The new compounds of the invention are optically active or racemic prostanoids of the following formula (I)

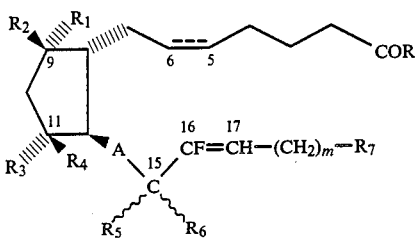

wherein
R is
(1) —OH or —OR', wherein R' is $C_1$-$C_6$ alkyl optionally substituted by phenyl or by a monocycloalkyl group or by a pentatomic or hexatomic heteromonocyclic ring containing at least one heteroatom chosen from O, S and N;
(2)

wherein each of R" and R''' is, independently, hydrogen; $C_1$-$C_6$ alkyl; phenyl; or a pentatomic or hexatomic heteromonocyclic ring containing at least one heteroatom chosen from O, S and N; or R" and R''', together with the nitrogen atom to which they are linked, form a pentatomic or hexatomic heteromonocyclic ring optionally containing a further heteroatom chosen from O, S and N;
(3) —W—$(CH_2)_n$—X wherein W is —O— or —NH—, n is an integer of 1 to 4 and X represents a group —OR' or a group

wherein R', R" and R''' are as defined above; or
(4) —$NHSO_2$—$R^{IV}$, wherein $R^{IV}$ is $C_1$-$C_4$ alkyl, phenyl or phenyl substituted by $C_1$-$C_4$ alkyl;
one of $R_1$ and $R_2$ is hydrogen and the other is hydroxy or $R_1$ and $R_2$, taken together, form an oxo group;
one of $R_3$ and $R_4$ is hydrogen and the other is hydroxy or $R_3$ and $R_4$ are both hydrogen or, taken together, form an oxo group;
one of $R_5$ and $R_6$ is hydroxy and the other is hydrogen, $C_1$-$C_6$ alkyl, $C_2$-$C_6$ alkenyl, $C_2$-$C_6$ alkynyl, or phenyl;
m is zero or an integer of 1 to 3;
$R_7$ is $C_1$-$C_6$ alkyl; $C_3$-$C_7$ monocycloalkyl; unsubstituted phenyl or phenyl substituted by one or more substituents chosen from $C_1$-$C_4$ alkyl, $C_1$-$C_4$ alkoxy, tri-halo-$C_1$-$C_4$-alkyl, halogen,

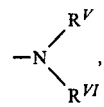

wherein each of $R^V$ and $R^{VI}$ is, independently, hydrogen, $C_1$-$C_4$ alkyl or phenyl; or $R_7$ is a pentatomic or hexatmoic heteromonocyclic ring containing at least one heteroatom chosen from O, S and N, and optionally substituted by one or more substituents chosen from halogen, $C_1$-$C_4$ alkyl, $C_1$-$C_4$ alkoxy, phenyl and phenoxy;
A is trans —CH=CH—, —$CH_2$—$CH_2$— or —C≡C—, and the symbol ---- represents a single bond or a cis double bond, with the condition that $R_3$ and $R_4$ do not form an oxo group when $R_1$ and $R_2$ form an oxo group.

The invention includes also the pharmaceutically or veterinarily acceptable salts of the compounds of formula (I) as well as all the possible isomers of formula (I), e.g. the optical antipodies, i.e. the enantiomers, and the racemic mixtures of the optical antipodies, the geometric isomers and their mixtures, the epimers and their mixtures, and the mixtures of the diastereoisomers. In particular, for example, as the double bond between the $C_{16}$ and the $C_{17}$ carbon atoms in formula (I) may be either in the Z (i.e. cis) or in the E (i.e. trans) configuration, it is intended that the invention comprises both the separated Z or E isomers and the Z,E mixtures, i.e. mixtures containing the Z isomers and the E isomers in any proportion.

In this specification the alkyl, alkenyl and alkynyl groups as well as the aliphatic moieties of the alkoxy groups may be branched or straight chain.

A $C_1$-$C_6$ alkyl group is, preferably, methyl, ethyl, n-propyl or tert-butyl.

A $C_1$-$C_4$ alkyl group is, preferably, methyl or ethyl.

A $C_2$-$C_6$ alkenyl group is, preferably, vinyl or allyl.

A $C_2$-$C_6$ alkynyl group is, preferably, ethynyl or propargyl.

A $C_1$-$C_4$ alkoxy group is, peferably, methoxy or ethoxy.

A tri-halo-$C_1$-$C_4$ alkyl group is, preferably, a tri-halomethyl group, trifluoromethyl in particular.

A halogen is, preferably, chlorine or bromine.

When, with reference to the definitions reported above for the formula (I) substituents, R is a group —OR', wherein R' is an unsubstituted $C_1$-$C_6$ alkyl this is, preferably, $C_1$-$C_4$ alkyl, in particular methyl or ethyl; when R' represents a $C_1$-$C_6$ alkyl substituted by a monocycloalkyl group, this is, preferably, a $C_3$-$C_7$ monocycloalkyl, in particular cyclopentyl or cyclohexyl. When R', or one of R" and R''', represents a $C_1$-$C_6$ alkyl group substituted by a pentatomic or hexatomic heteromonocyclic ring as reported above, the heteromonocyclic is, for example, furyl, tetrahydrofuryl, or pyridyl.

When R is a group

wherein each of R″ and R‴ is, independently, C₁–C₆ alkyl, the alkyl group is, preferably, C₁–C₄ alkyl, in particular methyl or ethyl.

When R is a group

wherein R″ and R‴, together with the nitrogen atom to which they are linked, form a pentatomic or hexatomic heteromonocyclic ring as defined above, this is, preferably, morpholino, thiomorpholino, piperidino or piperazino.

Preferred —OR′ groups are methoxy and ethoxy.
Preferred

groups are amino, dimethylamino and diethylamino.

When R is a group —W—(CH₂)ₙ—X as defined above, preferably W is —O—, n is 2 and X is —OR′, with R′ being C₁–C₄ alkyl, in particular methyl or ethyl.

A particularly preferred group —W—(CH₂)ₙ—X is ethoxy-ethoxy.

When R is a group —NH—SO₂—R$^{IV}$ as defined above, preferably R$^{IV}$ is C₁–C₄ alkyl, in particular methyl: a particularly preferred group —NH—SO₂—R$^{IV}$ is, indeed, methane-sulphonyl-amino.

When R₇ is C₁–C₆ alkyl, this is preferably, when m is zero, C₃–C₅ alkyl, in particular n-propyl, n-butyl or n-pentyl.

When R₇ is a C₃–C₇ monocycloalkyl group, this is, preferably, a C₅–C₇ monocycloalkyl, in particular cyclopentyl or cyclohexyl.

When R₇ is phenyl substituted as reported above, preferred substituents are trihalomethyl, in particular trifluoromethyl, and halogen, in particular chlorine.

When R₇ is a pentatomic or hexatomic heteromonocyclic ring as defined above, it may be either a saturated or an unsaturated ring.

Preferably it is an unsaturated pentatomic or hexatomic heteromonocyclic ring containing at least one heteroatom chosen from O, S and N.

When R₇ is an unsaturated pentatomic heteromonocyclic ring, it preferably contains one or two heteroatoms chosen from O, S and N and it is, in particular, furyl, thienyl, pyrrolyl or isoxazolyl; when R₇ is an unsaturated hexatomic heteromonocyclic ring, it preferably contains one or two nitrogen atoms and it is, in particular, pyridyl or pyrazinyl.

Preferably, in the above formula (I) R is (1) —OH or —OR′ wherein R′ is unsubstituted C₁–C₆ alkyl, in particular methyl or ethyl; (2)

wherein each of R″ and R‴ is, independently, hydrogen or C₁–C₆ alkyl, in particular methyl or ethyl; or (3) —W—(CH₂)ₙ—X wherein W is —O—, n is 2 and X is —OR′ with R′ as herein before defined.

Preferably R₁ is hydroxy and R₂ is hydrogen, or R₁ and R₂, taken together, form an oxo group; R₃ is hydroxy and R₄ is hydrogen, or R₃ and R₄ are both hydrogen; and one of R₅ and R₆ is hydroxy and the other is hydrogen. Preferably m is zero, and R₇ is (a) C₃–C₅ alkyl; or (b) C₅–C₇ monocycloalkyl, in particular cyclopentyl or cyclohexyl; or (c) phenyl optionally substituted by halogen or tri-halo-methyl, or (d) an unsaturated pentatomic or hexatomic heteromonocyclic ring containing one or two heteroatoms chosen from O, S and N.

Most preferably R is —OH or a group —OR′ wherein R′ is C₁–C₄ alkyl, in particular methyl or ethyl; and R₇ is phenyl optionally substituted by halogen, in particular chlorine, or by trihalomethyl, in particular trifluoromethyl.

Pharmaceutically or veterinarily acceptable salts of the compounds of formula (I) are either the salts with both inorganic and organic pharmaceutically or verterinarily acceptable bases, or the salts with both inorganic and organic pharmaceutically or veterinarily acceptable acids.

Inorganic bases are, for example, alkali metal, e.g. sodium or potassium, or alkaline earth metal, e.g. calcium or magnesium, hydroxides.

Organic bases are, for example, ammonium hydroxide and aliphatic or aromatic amines such as, for instance, triethylamine, trimethylamine, aniline and toluidine. Inorganic acids are, for example, hydrochloric, hydrobromic, sulphuric and phosphoric acid, and organic acids are, e.g., glycolic, lactic, oxalic, malonic, malic, maleic, tartaric, citric, fumaric, cinnamic, mandelic, salicylic, methanesulfonic and p-toluenesulfonic acid.

In the formulae of this specification a dashed line (∥∥∥∥) refers to a ring substituent in the α-configuration, i.e. to a substituent below the plane of the ring, and a wedge line (━■) refers to a ring substituent in the β-configuration, i.e. to a substituent above the plane of the ring. Similarly dashed lines (∥∥∥∥) and wedged lines (━■) indicate chain substituents in the α- and, respectively, in the β-configuration. A wavy line (∼∼∼) indicates that a substituent may be in the α- or in the β-configuration or both. Consequently, where a formula has a substituent with a wavy line bond, the formula may represent a compound having the substituent solely in the α-configuration or solely in the β-configuration, or the formula may represent a mixture of both compounds having the substituent in the α-configuration and compounds having the substituent in the β-configuration. Furthermore, the absolute "R" or "S" configurations of the chiral centers are assigned according to the sequence-rule procedure of IUPAC for the Nomenclature of Organic Chemistry (J.O.C. 35.9 2849, 1970). When unspecified the invention is meant to include both the single "R" or "S" epimers and their "R,S" mixtures.

A preferred class of compounds of the invention are the compounds of formula (I) wherein R is (1) —OH or —OR′ wherein R′ is C₁–C₆ alkyl; or (2)

wherein each of R" and R''' is, independently, hydrogen or $C_1$-$C_6$ alkyl; or (3) —W—$(CH_2)_n$—X wherein W is —O—, n is 2 and X is —OR' wherein R' is $C_1$-$C_6$ alkyl;

one of $R_1$ and $R_2$ is hydrogen and the other is hydroxy or $R_1$ and $R_2$, taken together, form an oxo group;

one of $R_3$ and $R_4$ is hydrogen and the other is hydroxy or $R_3$ and $R_4$ are both hydrogen;

one of $R_5$ and $R_6$ is hydrogen and the other is hydroxy;

m is zero;

$R_7$ is $C_3$-$C_5$ alkyl; $C_5$-$C_6$ cycloalkyl; unsubstituted phenyl or phenyl substituted by halogen or tri-halomethyl; or an unsaturated pentatomic or hexatomic heteromonocyclic ring containing one or two heteroatoms chosen from O, S and N;

A is —CH=CH-trans or —C≡C—; and the symbol ---- represents a cis-double bond or a single bond, and the pharmaceutically or veterinarily acceptable salts thereof.

In the above preferred class the $C_1$-$C_6$ alkyl groups are, preferably, $C_1$-$C_4$ alkyl groups and preferred $R_7$ values are n-propyl, n-butyl, n-pentyl, cyclopentyl, cyclohexyl, phenyl, chloro-phenyl, trifluoromethyl-phenyl, furyl, thienyl, pyrrolyl, isoxazolyl, pyridyl or pyrazinyl. A particularly preferred class of compounds of the invention are the compounds of formula (I) wherein R is —OH or —OR' wherein R' is $C_1$-$C_4$ alkyl;

$R_1$ is hydroxy and $R_2$ is hydrogen or $R_1$ and $R_2$, taken together, form an oxo group;

$R_3$ is hydroxy and $R_4$ is hydrogen or $R_3$ and $R_4$ are both hydrogen;

one of $R_5$ and $R_6$ is hydrogen and the other is hydroxy;

m is zero;

$R_7$ is phenyl, optionally substituted by a halogen atom or by a trifluoromethyl group;

A is —CH=CH-trans or —C≡C—; and the symbol ---- represents a cis-double bond or a single bond, and the pharmaceutically or veterinarily acceptable salts thereof.

In the above particularly preferred class, preferred A value is —CH=CH-trans.

Examples of specific compounds of the invention are:

5Z,13E,16Z-9α,11α,15R-trihydroxy-16-fluoro-prosta-5,13,16-trienoic acid and its methyl ester;

5Z,16Z-9α,11α,15R-trihydroxy-16-fluoro-prosta-5,16-dien-13-ynoic acid and its methyl ester;

5Z,13E,16Z-9α,11α,15R-trihydroxy-16-fluoro-18,19,20-trinor-17-cyclohexyl-prosta-5,13,16-trienoic acid and its methyl ester;

5Z,16Z-9α,11α,15R-trihydroxy-16-fluoro-18,19,20-trinor-17-cyclohexyl-prosta-5,16-dien-13-ynoic acid and its methyl ester;

5Z,13E,16Z-9α,11α,15R-trihydroxy-16-fluoro-18,19,20-trinor-17-phenyl-prosta-5,13,16-trienoic acid and its methyl ester;

5Z,16Z-9α,11α,15R-trihydroxy-16-fluoro-18,19,20-trinor-17-phenyl-prosta-5,16-dien-13-ynoic acid and its methyl ester;

5Z,13E,16Z-9α,11α,15R-trihydroxy-16-fluoro-18,19,20-trinor-17-(2'-furyl)-prosta-5,13,16-trienoic acid and its methyl ester;

5Z,16Z-9α,11α,15R-trihydroxy-16-fluoro-18,19,20-trinor-17-(2'-furyl)-prosta-5,16-dien-13-ynoic acid and its methyl ester;

5Z,13E,16Z-9α,11α,15R-trihydroxy-16-fluoro-18,19,20-trinor-17-(2'-thienyl)-prosta-5,13,16-trienoic acid and its methyl ester;

5Z,16Z-9α,11α,15R-trihydroxy-16-fluoro-18,19,20-trinor-17-(2'-thienyl)-prosta-5,16-dien-13-ynoic acid and its methyl ester;

5Z,13E,16Z-9-oxo-11α,15R-dihydroxy-16-fluoro-prosta-5,13,16-trienoic acid and its methyl ester;

5Z,13E,16Z-9-oxo-11α,15R-dihydroxy-16-fluoro-20-methyl-prosta-5,13,16-trienoic acid and its methyl ester;

5Z,13E,16Z-9-oxo-11α,15R-dihydroxy-16-fluoro-20-ethyl-prosta-5,13,16-trienoic acid and its methyl ester;

5Z,13E,16Z-9-oxo-11α,15R-dihydroxy-16-fluoro-18,19,20-trinor-17-phenyl-prosta-5,13,16-trienoic acid and its methyl ester;

5Z,13E,16Z-9-oxo-11α,15R-dihydroxy-16-fluoro-18,19,20-trinor-17-(2'-furyl)-prosta-5,13,16-trienoic acid and its methyl ester;

5Z,13E,16Z-9-oxo-11α,15R-dihydroxy-16-fluoro-18,19,20-trinor-17-(2'-thienyl)-prosta-5,13,16-trienoic acid and its methyl ester;

5Z,13E,16Z-9-oxo-11α,15R-dihydroxy-16-fluoro-18,19,20-trinor-17-(3'-pyridyl)-prosta-5,13,16-trienoic acid and its methyl ester;

13E,16Z-9-oxo-11α,15R-dihydroxy-16-fluoro-18,19,20-trinor-17-phenyl-prosta-13,16-dienoic acid and its methyl ester;

5Z,13E,16Z-9-oxo-15S-hydroxy-16-fluoro-18,19,20-trinor-17-phenyl-prosta-5,13,16-trienoic acid and its methyl ester;

5Z,13E,16Z-9-oxo-15R-hydroxy-16-fluoro-18,19,20-trinor-17-(2'-pyridyl)-prosta-5,13,16-trienoic cid and its methyl ester;

5Z,13E,16Z-9-oxo-15S-hydroxy-16-fluoro-18,19,20-trinor-17-(2'-pyridyl)-prosta-5,13,16-trienoic acid and its methyl ester;

5Z,13E,16Z-9-oxo-15R-hydroxy-16-fluoro-18,19,20-trinor-17-phenyl-prosta-5,13,16-trienoic acid and its methyl ester;

5Z,13E,16Z-9-oxo-15R-hydroxy-16-fluoro-prosta-5,13,16-trienoic acid and its methyl ester;

13E,16Z-9-oxo-15R-hydroxy-16-fluoro-18,19,20-trinor-17-phenyl-prosta-13,16-dienoic acid and its methyl ester, and the pharmaceutically or veterinarily acceptable salts of the free acids.

The compounds of formula (I) are prepared by a process comprising:

(1) submitting to reduction or Grignard reaction the $C_{15}$ carbonyl group of a compound of formula (II)

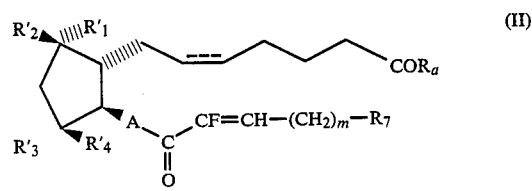

wherein

A, m and $R_7$ are as defined above;

$R_a$ is R, as defined above, or a group —OQ wherein Q is a protecting group for the carboxylic function;

one of $R'_1$ and $R'_2$ is hydrogen and the other is a free or protected hydroxy or $R'_1$ and $R'_2$, taken together, form a protected oxo group;

and one of $R'_3$ and $R'_4$ is hydrogen and the other is a free or protected hydroxy or $R'_3$ and $R'_4$ are both hydrogen or $R'_3$ and $R'_4$, taken together, form a protected oxo group, and, in any order, removing the protecting groups possibly present and, if desired, separating the obtained epimeric mixture of the 15S- and 15R-hydroxy compounds into the single epimers; or (2) selectively dehydrohalogenating a compound of formula (III)

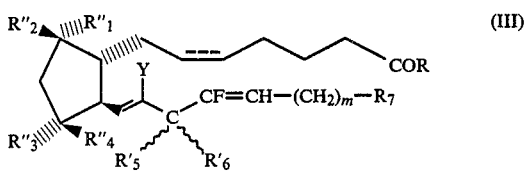

wherein

R, m and $R_7$ are as defined above, one of $R''_1$ and $R''_2$ is hydrogen and the other is a free or protected hydroxy or $R''_1$ and $R''_2$, taken together, form an oxo group; one of $R''_3$ and $R''_4$ is hydrogen and the other is a free or protected hydroxy or $R''_3$ and $R''_4$ are both hydrogen or, taken together, form an oxo group; one of $R'_5$ and $R'_6$ is a free or protected hydroxy and the other is hydrogen, $C_1$-$C_6$ alkyl, $C_2$-$C_6$ alkenyl, $C_2$-$C_6$ alkynyl or phenyl; and Y is chlorine, bromine or iodine, and removing the protecting groups possibly present, so obtaining a compound of formula (I) wherein A is —C≡C—; or (3) oxidizing a compound of formula (IV)

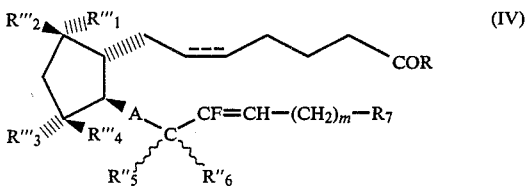

wherein

R, A, m and $R_7$ are as defined above; at least one of $R'''_1$, $R'''_2$, $R'''_3$ and $R'''_4$ is a free hydroxy group and the others of $R'''_1$, $R'''_3$ and $R'''_4$ have, respectively, the meanings reported above for $R''_1$, $R''_2$, $R''_3$ and $R''_4$, except oxo; one of $R''_5$ and $R''_6$ is hydrogen, $C_1$-$C_6$ alkyl, $C_2$-$C_6$-alkenyl, $C_2$-$C_6$ alkynyl or phenyl, and the other is a protected hydroxy, and removing the protecting groups, so obtaining, according to the used starting material, either a compound of formula (I) wherein $R_1$ and $R_2$, taken together, form an oxo group, or a compound of formula (I) wherein $R_3$ and $R_4$, taken together, form an oxo group, or a mixture of said oxidation products and, in this case, separating the obtained mixture into the individual oxidation products; or (4) reacting a compound of formula (V)

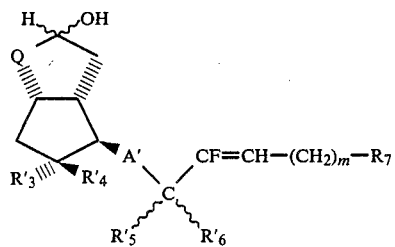

wherein $R'_3$, $R'_4$, $R'_5$, $R'_6$, m and $R_7$ are as defined above and A' is trans —CH=CH, —$CH_2$—$CH_2$—, —C≡C— or —CH=CY— wherein Y is as defined above, with a Wittig reagent comprising a group of formula —($CH_2$)$_4$—COR wherein R is as defined above, and removing the protecting groups possibly present, so obtaining a compound of formula (I) wherein the symbol ---- represents a cis double bond, $R_1$ is hydroxy and $R_2$ is hydrogen, and, if desired, converting the obtained compound into the corresponding compound of formula (I) wherein $R_1$ is hydrogen and $R_2$ is hydroxy, or into the corresponding compound of formula (I) where $R_1$ and $R_2$, taken together, form an oxo group; and, if desired, converting a compound of formula (I) wherein R is —OH and wherein the hydroxy groups present may be free or protected, or a reactive derivative thereof, into a compound of formula (I) wherein R is other than —OH through esterification or amidation reactions followed by removal of the protecting groups possibly present, and/or, if desired, salifying a compound of formula (I) or obtaining a free compound of formula (I) from a salt thereof, and/or, if desired, separating a mixture of isomers of formula (I) into the single isomers. The limitative condition previously reported with respect to the substituents $R_1$, $R_2$, $R_3$ and $R_4$ of formula (I) in order to exclude the simultaneous presence of an oxo group at the positions 9 and 11, applies also to the corresponding 9- and 11- substituents of the other formulae of this specification, e.g. the above formulae (II) to (IV), so that the contemporary presence of a free or protected oxo group at both the 9- and the 11-position is to be regarded as excluded in all cases.

In the above formulae (II) to (V) a protected hydroxy group is an etherified or esterified hydroxy group easily convertible to free hydroxy group under mild, either acidic or basic, conditions.

Examples of etherified hydroxy groups are silyl ethers: for instance trialkylsilyl ethers such as, e.g., trimethyl-, dimethyl-tert-butyl-; dimethyl-isopropyl; or dimethylethylsilyl ether; and also acetal and enol ethers: for instance, tetrahydropyranyl ether, tetrahydrofuranyl ether, dioxanyl ether, oxathianyl ether, or one of the following

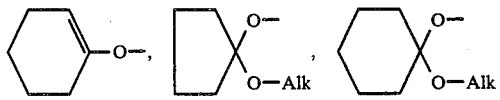

where Alk is $C_1$-$C_6$-alkyl.

Examples of esterified hydroxy groups are aliphatic or aromatic carboxylic $C_2$-$C_{10}$ acyloxy groups such as, e.g., acetoxy, benzoyloxy or substituted benzoyloxy, e.g. p-nitro-benzoyloxy.

A protected oxo group is an oxo group protected, e.g., as acetal, thioacetal, ketal or thioketal, in particular, for example, as dimethoxy acetal, dimethylthioacetal ethylenedioxyketal or ethylenedithioketal.

A protecting group (Q) for the carboxylic function may be any known carboxy protecting group easily removable under mild conditions, such as, for instance, tetrahydropyranyl or trimethylsilyl.

The reduction of the $C_{15}$ carbonyl group of a compound of formula (II) may be carried out by any reducing agent which is suitable for reducing ketones to alcohols in particular, for example, a boron or aluminium hydride complex such as, e.g., sodium boron hydride, lithium boron hydride, zinc boron hydride, tri-isobutyl boron hydride, tri-isobutyl potassium boron hydride, or a tri-$C_1$-$C_6$-alkoxy aluminium hydride, e.g. tri-tert-butoxy-aluminium hydride.

Any suitable anhydrous or aqueous organic solvent may be used for the reduction, for instance diethyl ether, tetrahydrofuran, dioxane, dimethoxyethane, methanol or their mixtures; any temperature between about $-40°$ C. and the boiling point of the solvent may be employed, preferred temperatures being between about $-25°$ C. and about $+25°$ C. The optional separation of the obtained mixture of the 15S and 15R epimeric secondary alcohols may be performed by fractional crystallization or by chromatography, for instance column cromatography, e.g. silica gel chromatography or HPLC preparative chromatography, or preparative TLC, using as eluant an appropriate mixture of solvents preferably chosen from the group consisting of methylene chloride, diethyl ether, ethyl acetate, n-hexane and cyclohexane.

The removal of the possibly present protecting groups, either on the mixture of the 15R and 15S alcohols, or on a separated 15R or 15S alcohol may be carried out in a conventional manner.

Thus, for example, the ether protecting groups may be removed from the hydroxyl functions with mild acid hydrolysis, for instance with mono- or poly-carboxylic acids like acetic, formic, citric, oxalic, or tartaric in a solvent like water, acetone, tetrahydrofuran, dimethoxyethane or a low molecular weight aliphatic alcohol, or with a sulfonic acid like p-toluene-sulfonic in a low molecular weight alcohol like anhydrous ethanol or methanol, or with a polystyrene-sulfonic resin.

For example, a 0.1–0.25N polycarboxylic acid (like oxalic or citric) is used with a suitable low-boiling solvent miscible with water and readily removable under vacuum at the end of the reaction.

Silyl ether residues may also be removed with F$^-$ ions in solvents like tetrahydrofuran and dimethylformamide. Ester protecting groups, including carboxy protecting groups, may be, e.g., removed by following known saponification procedures, generally under mild basic conditions.

Ketal and thioketal protecting groups are generally removed by mild acid hydrolysis as described above. The Grignard reaction on the $C_{15}$ carbonyl group of a compound of formula (II) may be carried out reacting the compound of formula (II) with a Grignard reagent of formula $R_8MgY$ wherein $R_8$ is $C_1$-$C_6$ alkyl, $C_2$-$C_6$ alkenyl, $C_2$-$C_6$ alkynyl or phenyl and Y is as defined above. The reaction is preferably performed in an anhydrous solvent, such as, for instance, diethyl ether, tetrahydrofuran, dioxane, dimethylsulphoxide, benzene or toluene, at a temperature which may vary from about $-70°$ C. to the boiling point of the solvent, preferred temperatures being from about $-60°$ C. to about $+20°$ C.

The initially formed organometallic complex may be decomposed by hydrolysis using, e.g., saturated aqueous ammonium chloride according to conventional procedures. The optional separation of the obtained mixture of the 15S and 15R epimeric tertiary alcohols, and the removal of the protecting groups possibly present may be performed as indicated hereabove with regard to the reduction of the compound of formula (II).

The selective dehydrohalogenation of a compound of formula (III) may be carried out by treatment with a base preferably chosen from an alkali metal amide, e.g. sodium amide, an alkali metal alkoxide, e.g. potassium tert. butoxide, diazabicycloundecene, diazabicyclononene and the $CH_3-SO-CH_2^{(-)}$anion. The reaction is preferably carried out in an oxygen-free atmosphere in an inert aprotic solvent such as, e.g., dimethylsulphoxide, dimethylformamide, hexamethylphosphoramide, dioxane, tetrahydrofuran, benzene and the like, at a temperature ranging from about $-60°$ to about $100°$ C., the room temperature being the preferred one.

The subsequent removal of the protecting groups present, if any, may be performed as previously indicated. The oxidation of a compound of formula (IV) may be carried out by means of oxidizing agents such as, for example, $CrO_3$ or the Jones reagent (G. I. Poos and al. J.Am.Chem.Soc. 75, 422, 1953) or the Moffatt reagent (J. Am.Chem.Soc. 87, 5661, 1965), operating in a suitable solvent which may be, for example, acetone, dioxane, benzene or dimethylsulphoxide at a temperature which may vary from the room temperature to the boiling point of the used solvent. For the oxidation the procedure described in Tetr. Lett. 2235, 1974, may also be followed. Again the subsequent removal of the protecting groups may be performed as reported before. The separation of a possibly obtained mixture of oxidation products may be carried out, e.g., by chromatography or by fractional crystallization. The Wittig reagent used for the reaction with a compound of formula (V) may be a compound of formula

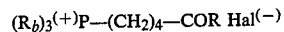

$(R_b)_3^{(+)}P-(CH_2)_4-COR\ Hal^{(-)}$ wherein R is as defined above, Hal is bromine or chlorine and $R_b$ is $C_1$-$C_6$ alkyl or phenyl.

The preparation of the Wittig reagent is discussed in detail by Tripett, Quart. Rev., 1963, XVII, No 4, 406. The reaction between a compound of formula (V) and the Wittig reagent may be performed using a slight excess of the Wittig reagent per mole of lactol (V), operating in an inert organic solvent such as, e.g., diethyl ether, tetrahydrofuran, n-hexane, dimethylsulphoxide, dimethylformamide or hexamethylphosphoramide, in the presence of a base which may be, for instance, sodium hydride or potassium tert.butoxide.

The temperature may vary between about 0° C. and the reflux temperature of the reaction mixture, although the reaction is preferably performed at room temperature or below.

When for the reaction with the Wittig reagent a compound of formula (V) is used wherein A' is —CH=CY—, with Y as defined above, about two moles of Wittig reagent are preferably employed per mole of compound (V) so that simultaneous dehydrohalogenation takes place on A' to give compounds of formula (I) wherein A is —C≡C—. Dehydrohalogenation on A' proceeds selectively with respect to the fluorinated double bond at the $C_{16}$–$C_{17}$ position.

The subsequent removal of the protecting groups possibly present may be carried out as previously indicated. The optical conversion of an obtained compound of formula (I) wherein $R_1$ is hydroxy and $R_2$ is hydrogen into one wherein $R_1$ is hydrogen and $R_2$ is hydroxy may be performed following the procedures described, e.g., in U.K. patent specification No. 1498105, while the optional conversion of the same compound into one wherein $R_1$ and $R_2$, taken together, form an oxo group, may be carried out using analogous conditions as those previously reported for the oxidation of a compound of formula (IV). A reactive derivative of a compound of formula (I) wherein R is OH may be, for example, an ester thereof, e.g. a $C_1$–$C_6$ alkyl ester, or an acyl halide, e.g., the chloride, or the anhydride or a mixed anhydride thereof.

The optional conversion of a compound of formula (I) wherein R is OH, or a reactive derivative thereof, into a corresponding compound wherein R is other than OH through esterification and amidation reactions may be performed according to conventional methods.

For example, a compound of formula (I) wherein R is OH may be converted into a compound of formula (I) wherein R is —OR′ where R′ is as defined above by the known procedures reported in the organic chemistry for the esterification of a carboxylic acid. The carboxylic acid or a reactive derivative thereof such as, for instance, an acyl halide, e.g. the chloride, or the anhydride or a mixed anhydride, or the corresponding azide may be, e.g., reacted with an alcohol of formula R′OH, where R′ is as defined above, operating either at room temperature or under cooling in a suitable solvent such as, e.g., dioxane, tetrahydrofuran, benzene, toluene, chloroform, methylene chloride, dimethylformamide, and, if necessary, according to the starting material used, either in the presence of a condensing agent such as, for instance, a carbodiimide, e.g. dicyclohexylcarbodiimide, carbonyldiimidazole and the like, or in the presence of a base which may be, for instance, sodium bicarbonate or carbonate, potassium carbonate or bicarbonate, an organic amine, e.g. triethylamine, or another acid acceptor such as, e.g., an anionic exchange resin.

In analogous fashion a compound of formula (I) wherein R is OH may be converted into a compound of formula (I) wherein R is —W—$(CH_2)_n$—W wherein W, n and X are as defined above. In particular, for example, this conversion may be carried out reacting a compound of formula (I) where R is OH with a compound of formula H—W—$(CH_2)_n$—X in the presence of a dehydrating agent, e.g. one of those hereabove indicated, operating in an inert solvent such as, e.g. chloroform, methylene chloride, diethyl ether, tetrahydrofuran, dimethylformamide, benzene, toluene, n-pentane, n-hexane and the like and, if desired, in the presence of a suitable acylation catalyst, e.g. pyridine or 4-dimethylamino pyridine (DMAP).

The reaction is conveniently made in two steps wherein the first step is the preparation of the substituted isourea derivative of formula (VI)

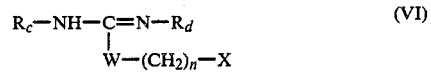

(VI)

wherein W, n and X are as defined above and each of $R_c$ and $R_d$ is, independently, an optionally substituted $C_1$–$C_6$ alkyl radical, e.g. ethyl, isopropyl, 3-dimethylaminopropyl, or a cycloalkyl radical, e.g. cyclohexyl; and wherein the second step is the reaction of this compound with the compound of formula (I).

The conversion of a compound of formula (I) wherein R is OH into a compound of formula (I) wherein R is OR′ wherein R′ is $C_1$–$C_6$ alkyl may also be performed through reaction with the appropriate diazo-$C_1$–$C_6$ alkane, e.g. diazomethane, diazoethane and the like, preferably operating at room temperature or under cooling, in an anhydrous organic solvent chosen, e.g., from the group of diethyl ether, tetrahydrofuran or dioxane.

The conversion of a compound of formula (I) wherein R is OH into a compound of formula (I) wherein R is

wherein R″ and R‴ are as defined above, may be carried out reacting a reactive derivative of the compound of formula (I), e.g. a $C_1$–$C_6$ alkyl ester thereof, e.g. the methyl or ethyl ester, or an acyl halide, e.g. the chloride, with the appropriate amine of formula

The reaction may be, for instance, carried out in an inert solvent such as, e.g. benzene, toluene, methanol, ethanol, diethyl ether, tetrahydrofuran or dimethylformamide, at any suitable temperature between the room temperature and the boiling point of the solvent.

When, an acyl halide, e.g. the chloride, of a compound of formula (I) where R is OH is used for the reaction with the amine, then the presence of a base preferably an inorganic base such as, e.g., sodium carbonate or bicarbonate, is required and preferred solvents are, in this case, benzene or toluene.

In particular, a compound of formula (I) where R is

wherein R″ and R‴ are both hydrogen may be obtained from a $C_1$–$C_6$ alkyl ester, e.g. the methyl or ethyl ester, of a compound of formula (I) where R is OH, reacting the ester with gaseous ammonia in a lower aliphatic alcohol in a conventional manner.

Analogous procedures as those hereabove described for obtaining a compound of formula (I) where R is

from a compound of formula (I) wherein R is OH may be followed also for obtaining a compound of formula (I) wherein R is —$NHSO_2$—$R^{IV}$, where $R^{IV}$ is as defined above, from a compound of formula (I) wherein R is OH.

The optical salification of a compound of formula (I) and the preparation of a free compound of formula (I) from a salt thereof may be carried out by standard procedures.

Also the optional separation of a mixture of isomers of formula (I) into the single isomers may be performed in a conventional manner e.g. by fractional crystallization or by chromatography as previously reported in this specification.

The compounds of formula (II) may be obtained reacting a compound of formula (VIII)

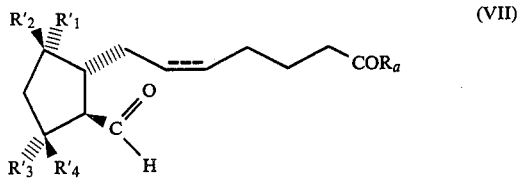
(VII)

wherein $R_a$, $R'_1$, $R'_2$, $R'_3$ and $R'_4$ are as defined above, with a compound of formula (VIII)

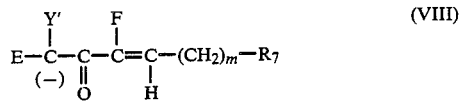
(VIII)

wherein m and $R_7$ are as defined above, Y' is hydrogen, bromine, chlorine or iodine, and E is a group $(C_6H_5)_3P^{(+)}$- or a group

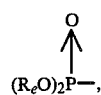

wherein each $R_e$ is, independently, $C_1$-$C_6$ alkyl or phenyl, so obtaining a compound of formula (IX)

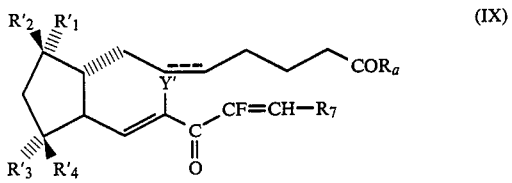
(IX)

wherein $R_a$, $R'_1$, $R'_2$, $R'_3$, $R'_4$, Y' and $R_7$ are as defined above, and selectively dehydrohalogenating a compound of formula (IX) where Y' is bromine, chlorine or iodine, so obtaining a compound of formula (II) where A is —C≡—, or selectively hydrogenating a compound of formula (IX) wherein Y' is hydrogen so obtaining a compound of formula (II) where A is —CH$_2$—CH$_2$—, and, if desired, removing the protecting groups possibly present.

The selective dehydrohalogenation of a compound of formula (IX) where Y' is bromine, chlorine or iodine may be carried out as previously reported for the selective dehydrohalogenation of a compound of formula (III). The selective hydrogenation of a compound of formula (IX) where Y' is hydrogen may be carried out catalytically, e.g. in the presence of palladium on charcoal, with the stoichiometric amount of hydrogen. The subsequent optional removal of the hydroxy protecting groups may be performed as indicated above in this specification.

The compounds of formula (III) may be prepared submitting to reduction or Grignard reaction the $C_{15}$ carbonyl group of a compound of formula (IX) wherein Y' is chlorine, bromine or iodine and, in any order, removing the oxo protecting group possibly present and, if desired, protecting the free hydroxy group at the $C_{15}$ position and/or the other free hydroxy groups possibly present or, if desired, removing the hydroxy protecting groups possibly present.

The reduction and the Grignard reaction on a compound of formula (IX) may be carried out as indicated before with reference to the conversion of a compound of formula (II) in to a compound of formula (I).

The removal of the oxo- and hydroxy-protecting groups possibly present in the obtained compound may be performed as previously reported, and the optional protection of the free hydroxy groups may be carried out according to known conventional procedures.

The compound of formula (IV) may be prepared following known and conventional procedures, from compounds of formula (I) or derivatives thereof wherein the hydroxy and/or oxo groups are in a protected form.

Thus, for example, a compound of formula (IV) wherein one of $R'''_1$ and $R'''_2$ is a free hydroxy group and the other substituents are as defined above with reference to formula (IV), may be obtained etherifying a compound of formula (X).

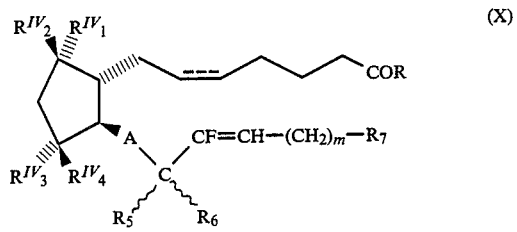
(X)

wherein R, A, $R_5$, $R_6$, m and $R_7$ are as defined above; one of $R^{IV}_1$ and $R^{IV}_2$ is hydrogen and the other is an esterified hydroxy group, e.g. a $C_2$-$C_{10}$ carboxylic acyloxy group as defined above, in particular acetoxy or benzoyloxy or p-nitro-benzoyloxy; one of $R^{IV}_3$ and $R^{IV}_4$ is hydrogen and the other is an etherified hydroxy, e.g. a silyloxy group or tetrahydropyranyloxy group, or $R^{IV}_3$ and $R^{IV}_4$ are both hydrogen, so obtaining a compound of formula (XI)

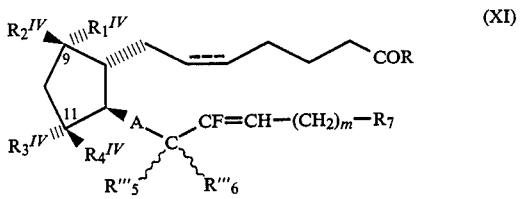
(XI)

wherein R, $R^{IV}_1$, $R^{IV}_2$, $R^{IV}_3$, $R^{IV}_4$, A, m and $R_7$ are as defined above and one of $R'''_5$ and $R'''_6$ is an etherified hydroxy and the other is hydrogen, $C_1$-$C_6$ alkyl, $C_2$-$C_6$ alkenyl, $C_2$-$C_6$ alkynyl or phenyl, and then de-esterifying, e.g. de-acylating, at the $C_9$ position the obtained compound of formula (XI).

In analogous fashion a compound of formula (IV) wherein one of $R'''_3$ and $R'''_4$ is hydroxy and the other substituents are as defined above may be prepared etherifying a compound of formula (XII)

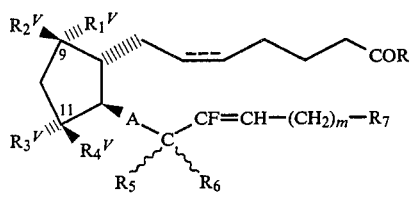

wherein R, A, R$_5$, R$_6$, m and R$_7$ are as defined above; one of R$^V_1$ and R$^V_2$ is hydrogen and the other is an etherified hydroxy, e.g. a silyloxy group or tetrahydropyranyloxy, and one of R$^V_3$ and R$^V_4$ is hydrogen and the other is an esterified hydroxy, e.g. a C$_2$–C$_{10}$ carboxylic acyloxy, in particular acetoxy, benzoyloxy or p-nitro-benzoyloxy, so obtaining a compound of formula (XIII)

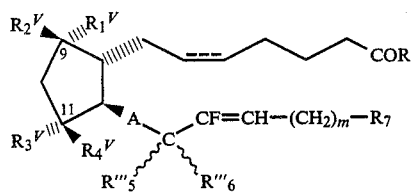

wherein R, R$^V_1$, R$^V_2$, R$^V_3$, R$^V_4$, A, R'''$_5$, R'''$_6$, m and R$_7$ are as defined above, and then de-esterifying, e.g. de-acylating, the obtained compound of formula (XIII) at the C$_{11}$ position.

The above mentioned etherification processes, e.g. the etherification of a compound of formula (X) and the etherification of a compound of formula (XII) may be carried out in a known manner, e.g. through reaction with a chlorosilane in the presence of a base, for instance imidazole or a trialkylamine, e.g. triethylamine, in order to obtain a silyl ether, or through reaction with dihydropyran in the presence of catalytic amounts of, e.g., p-toluene-sulfonic acid, in order to obtain a tetrahydropyranyl ether.

The above said de-esterification, e.g. de-acylation, processes, as those carried out, for instance, on the compounds (XI) and (XIII), may be performed in a known manner too, generally operating under mild basic conditions, for example by reaction with an alkali metal hydroxide, e.g. sodium hydroxide, in an aqueous-alcoholic medium; or by transesterification in an appropriate dry alcohol, in the presence of a basic catalyst such as, e.g. an alkali metal carbonate, e.g. sodium carbonate, under nitrogen atmosphere at room temperature.

A compound of formula (V) may be prepared reducing a compound of formula (XIV)

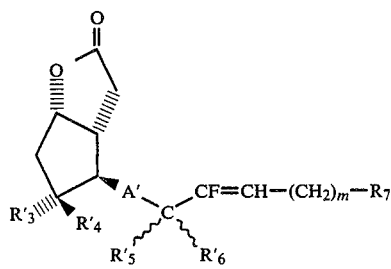

wherein R'$_3$, R'$_4$, A', R'$_5$, R'$_6$, m and R$_7$ are as defined above. The reduction may be, e.g., performed by treatment with diisobutyl aluminium hydride or sodium bis-(2-methoxy-ethoxy)-aluminum hydride in an inert solvent, for example, toluene, n-heptane, n-hexane or benzene or their mixtures, at below 30° C.

The compounds of formula (VII) are known compounds [T. S. Bindra and R. Bindra, Prostaglandin Synthesis, Acad. Press. New York, 1977, 236], or may be prepared by known methods from known compounds.

A halocarbanion compound of formula (VIII) may be prepared by treatment of a compound of formula (XV)

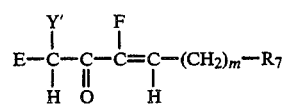

wherein E, Y', m and R$_7$ are as defined above, with an equivalent amount of a base which is preferably selected from sodium hydride, lithium hydride, calcium hydride, a C$_1$–C$_6$ alkyl, e.g. methyl, lithium derivative, or an alkali metal, e.g. sodium, methylsulfonyl methide. A compound of formula (XV) wherein Y' is chlorine, bromine or iodine may be obtained halogenating a carbanion of formula (XVI)

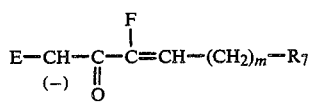

wherein E, m and R$_7$ are as defined above.

The halogenation may be carried out in a conventional manner using a halogenating agent selected, e.g., from the group of N-chloroacetamide, N-bromoacetamide, N-chlorosuccinimide, N-bromosuccinimide, 2-pyrrolidine hydrotribromide, pyridine hydrotribromide and the like.

A compound of formula (XV) wherein Y is hydrogen may be obtained, according to reaction conditions well known to the skilled in the art, from a fluoro acid of formula (XVII)

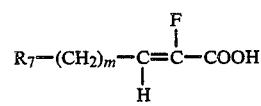

wherein R$_7$ and m are as defined above.

The compounds of formula (XVII) are known compounds [Milos Hudlicky, Chemistry of Organic Fluorine Compounds, John Wiley and Sons, 347], or may be prepared by known methods from known compounds.

The compounds having the formulae (X) and (XII) may be prepared following procedures which are usual in the prostaglandin chemistry, for instance through esterification and etherification reactions carried out on a corresponding formula (I) compound, or through a reaction between an aldehyde corresponding to one of formula (VII), wherein, however, $R'_1$, $R'_2$, $R'_3$ and $R'_4$ have the meanings given for the corresponding substituents in the formulae (X) and (XII), and a compound of formula (VIII).

The compound of formula (XIV) may be prepared too following procedures well known in the prostaglandin chemistry, for example those described in U.K. patent specification no. 1493557 for the synthesis of analogous compounds.

The compounds having the formulae (II), (III), (IV), (X), (XI), (XII) and (XIII) are a further object of the present invention.

The compounds of formula (I) may be used on mammals in all the conditions where natural prostaglandins are indicated, and administered by the usual routes, e.g. orally, parenterally, rectally, intravaginally, or by aerosol, with the advantages of a superior resistence to the enzyme 15-prostaglandin dehydrogenase which, as is known, rapidly inactivates natural prostaglandins.

The compounds of formula (I) are also endowed with more lasting therapeutic activity than natural prostaglandins, when administered by usual routes and especially when administered by oral route.

Furthermore the prostanoids of formula (I) are more potent in biological responses and have a narrower spectrum of biological potency than the known prostaglandins, showing more specificity in their activity and causing smaller and fewer undesired side-effects. Thus, for example, the compounds of formula (I), in particular the 9α-hydroxy derivatives, exhibit a remarkable luteolytic activity and, therefore, they may be used in fertility control with the advantage of a considerably reduced ability to stimulate the smooth muscles. The side-effects of the natural prostaglandins, like, e.g., vomiting and diarrhea, are completely or almost completely absent. The luteolytic activity of the compounds of the invention was evaluated, for instance, in hamsters according to the procedure reported by A. B. Labhstwar in Nature, 230, 528, 1971.

Following the said procedure, for example, the activity in hamster luteolysis of the 16-fluoro-16, 17 unsaturated compound of the invention 5Z,13E,16Z-9α,1-1α,15R-trihydroxy-16-fluoro-18,19,20-trinor-17-phenyl-prosta-5,13,16-trienoic acid methyl ester was compared with the activity of the close "erythro" and "threo" 16-fluoro-16,17-saturated analogs: 5Z,13E-9α,11α,15R-trihydroxy-16S-fluoro-18,19,20-trinor-17-phenyl-prosta-5,13-dienoic acid methyl ester and, respectively, 5Z,13E-9α,11α,15R-trihydroxy-16R-fluoro-18,19,20-trinor-17-phenyl-prosta-5,13-dieonic acid methyl ester.

The same compounds were also compared as regards the Guinea pig ileum contracting activity according to the following procedure:

ileum segments obtained from male Guinea pig were placed under 0.5 g tension in a 10 ml thermostatic bath held at 35° C., containing Tyrode solution gassed with a mixture of $O_2$ and $CO_2$. The tissue was left 30 minutes to stabilize before the compounds were tested. The response was recorded using an isotonic transducer. Log-dose response curves of the tested compounds were compared.

The results of the comparisons, expressed in term of potency ratio with respect to $PGF_{2\alpha}$, are reported in the following Table I wherein the compound (A) is the compound of the invention and the compounds (B) and (C) are the reference compounds.

TABLE I

| COMPOUNDS | IN VIVO | IN VITRO |
|---|---|---|
| (structure with OH, COOCH3, L) | hamster luteolysis potency ratio Vs $PGF_{2\alpha}$ = 1 | guinea pig ileum potency ratio Vs $PGF_{2\alpha}$ = 1 |
| (A): L = (structure with F, OH, H) | 120 | 0.4 |
| (B): L = (structure with F, OH) ("erythro") | 24 | 0.5 |
| (C): L = (structure with F, OH) ("threo") | 0.96 | 0.2 |

It is evident from the reported data that a remarkable increase of the luteolytic activity is achieved with the compound of the invention while a reduced stimulating activity on ileum is maintained, with respect to the $PGF_{2\alpha}$ standard, indicating a low incidence of the undesired gastrointestinal side effects. Moreover the results summarized in the above table are even more significant in that they are unexpected and surprising.

It is reported indeed [Advance in Prostaglandins and Thromboxane Researches 6, 365, 1975] that, in the series of the 16-fluoro-16,17-saturated prostaglandins, the relative configuration between the 16-fluoro atom and the 15-hydroxy group plays an essential role for the development of the luteolytic activity, with this activity developing at a greater extent in the "erythro" compounds than in the "threo" compounds. As a consequence one would expect that the destruction of said relative configuration is accompanied by a decrease in luteolytic activity.

Surprisingly, on the contrary, the introduction of a double bond between the 16 and 17 positions of a 16-fluoro prostaglandin, with consequent destruction of the above said "relative configuration", produces a remarkable increase in luteolytic activity: in fact the 16-fluoro-16,17 unsaturated compounds of formula (I) have been found to be more potent than the 16-fluoro-16,17 saturated analogs, not only with respect to the less active "threo" compounds but also with respect to the more active "erythro" ones.

For the use as luteolytic agents the compounds of formula (I) may be, e.g., administered orally, parenterally or by intraenous or intrauterine way. For instance they can be administered by intravenous infusion of a sterile isotonic saline solution at a dose of about 0.001 to 5, preferably 0.005 to 1 μg/kg of mammal body weight per minute, the exact dose depending on the conditions of the patient to be treated. Furthermore, the compounds of formula (I), particularly the 9-oxo derivatives, produce strong uterine contraction, as is proved by the fact that they have been found to be active in the in vitro uterus contraction test [Pharm. Res. Comm. vol. 6, 5, 437–444, 1974] and in vivo on the ovariectomized rabbit [R. D. Heilman, S. M. Strainer, Prostaglandins 12, 1, 127, 1976]. When Guinea pigs were given prostaglandins derivatives of the present invention, on days 43 and 44 of gestation complete abortion was noted at doses from 0.001 to 0.03 mg/kg twice a day.

For instance, when the compound 5Z, 13E,16Z-9-oxo-11α,15R-dihydroxy-16-fluoro-18,19,20-trinor-17-phenyl-prosta-5,13,16-trienoic acid methyl ester was used, a dose of 0.001 mg/kg twice a day was found to induce complete abortion in four out of five Guinea pigs. When the 11-deoxy analog 5Z,13E,16Z-9-oxo-15R-hydroxy-16-fluoro-18,19,20-trinor-17-phenyl-prosta-5,13,16-trienoic acid methyl ester was used, a dose of 0.003 mg/kg twice a day was found to induce complete abortion in four out of ten Guinea pigs, while the fully effective dose (complete abortion in all tested animals) was 0.03 mg/kg twice a day.

For the reference natural PGE$_2$ the fully effective dose was 0.3 mg/kg twice a day and a dose of 0.1 mg/kg twice a day was required to produce abortion in two out of six animals.

In view of the above indicated activities the compounds of the invention can be used, e.g., to control the reproductive cycle in menstruating females mammals, including humans; to cause cervical dilation in pregnant and non-pregnant female mammals for gynaecology and obstetrics; to induce labor or clinical abortion or expel a dead fetus in pregnant females, both in humans and in mammals.

In these applications the compounds can be administered, for example, by intravenous infusion, e.g. at a dose of approximately 0.001 mg/kg minute until the end of labor; orally at a single or multiple doses from about 0.1 mg to about 5 mg per dose; intramuscularly at a single or multiple doses from about 0.01 mg to about 1 mg per dose; or intravaginally at a single or multiple doses from about 0.05 mg to about 10 mg per dose.

Another useful pharmacological property of the compounds of formula (I), particularly the 9-oxo derivatives, is their anti-ulcerogenic activity, as is proved by the fact that they have been found to be active in preventing stress-induced or ASA-induced gastric ulcers and indomethacin induced intestinal ulcers [Prostaglandins and Medicine vol. 5, 131–139, 1980], and in inhibiting gastric secretion according to the method of Shay et al. [Gastroenter. 26, 906, 1954].

In view of this activity the compounds of formula (I) can be useful to reduce and control excessive gastric secretion in mammals and therefore to reduce or eliminate the formation of gastrointestinal ulcers and, at the same time, they are able to accelerate the healing process of any ulcers already present in the gastrointestinal tract. The compounds of formula (I) can consequently be used also for reducing the undesirable gastrointestinal side-effects resulting from systemic administration of anti-inflammatory prostaglandin synthetase inhibitors and may be, therefore, used for this purpose in association with them.

The compounds of formula (I) in accordance with these purposes can be, e.g., administered orally, parenterally, e.g. by intravenous injection or infusion, or by intramuscolar injection, or rectally. When administered orally the compounds of the invention may be used at a dosage ranging from about 1 mg to about 10 mg, preferably 5 mg, once or three times a day. In intravenous infusion, the dosage varies from approximately 0.01 µg to 0.05 µg per kilogram of body weight per minute.

The total daily dose, both by injection and by infusion, may vary from about 0.1 to about 20 mg. Of course, in the treatment of the above conditions, the exact treatment level depends on the case history of the patient to be treated.

The compounds of formula (I), in particular the 9-oxo and 11-oxo derivatives, were also found to inhibit at low dosages the platelet aggregation induced in vitro by 0.4 µg/ml ADP in Guinea-pig platelet rich plasma, and so they are also antiaggregating agents useful to inhibit platelet aggregation, to decrease adhesion, to prevent clot formation and, generally, to treat conditions of hyperlipidaemia such as, for instance, atheroscelerosis and arteriosclerosis.

The compounds of formula (I), particularly the 9-oxo and 11-oxo derivatives, can be used also as antineoplastic agents, as is proved, e.g., by the fact that they were found to be active in inhibiting B-16 melanoma growth in vitro and in vivo tests. Thus, for example, in vivo experiments carried out on mice intraperitoneally treated for 4 consecutive days with the compounds of the invention at daily doses varying from 0.25 to 5 mg/kg, according to Hofer et al, J. Surg. Res. 32, 552, 1982, showed an evident and significant inhibition of the tumor growth. The toxicity of the compounds of the invention was found to be quite negligible and therefore they can be safely used in therapy.

The pharmaceutical compositions of the invention are usually prepared following conventional methods and are administered in a pharmaceutically suitable form. For example, the solid oral forms may contain, together with the active compound, diluents, e.g., lactose, dextrose, saccharose, cellulose, corn starch and potato starch; lubricants, e.g. silica, talc, stearic acid, magnesium or calcium stearate, and/or polyethylene glycols; binding agents, e.g. starches, arabic gums, gelatin, methylcellulose, carboxymethyl cellulose, polyvinylpyrrolidone; disaggregating agents, e.g. a starch, alginic acid, alginates, sodium starch glycolate; effervescing mixtures; dyestuffs, sweeteners; wetting agents, for instance, lecithin, polysorbates, laurylsulphates; and, in general, non-toxic and pharmacologically active substances used in pharmaceutical formulations. Said pharmaceutical preparations may be manufactured in known manner, for example, by means of mixing, granulating, tabletting, sugar-coating, or film-coating processes. The liquid dispersions for oral administration may be, e.g., syrups, emulsions and suspensions.

The syrups may contain as carrier, for example, saccharose or saccharose with glycerine and/or mannitol and/or sorbitol; in particular a syrup to be administered to diabetic patients can contain as carriers only products not metabolizable to glucose, or metabolizable in very small amount to glucose such as, sorbitol. The suspensions and the emulsions may contain as carrier, for example, a natural gum, agar, sodium alginate, pectin, methylcellulose, carboxymethylcellulose, or polyvinyl alcohol.

The suspensions or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride. The solutions for intravenous injections or infusions may contain as carrier, for example, sterile water or, preferably, they may be in the form of sterile aqueous isotonic saline solutions.

The suppositories and the vaginal tablets may contain, together with the active compound, a pharmaceutically acceptable carrier, e.g. cocoa-butter, polyethylene glycol, a polyoxyethylene sorbitan fatty acid ester surfactant or lecithin.

This invention is illustrated but not limited by the following examples wherein the abbreviations DHP, THF, THP, DMSO, DIBA, DCC and HPLC stand, respectively, for dihydropyran, tetrahydrofuran, tetrahydropyran, dimethylsulphoxide, diisobutylaluminium hydride, dicyclohexylcarbodiimide and high performance liquid chromatography.

Where unspecified, the $[\alpha]$ values refer to C=1 concentrations in ethanol.

EXAMPLE 1

Under a nitrogen atmosphere, to a stirred slurry of 0.290 g of 80% NaH (dispersion in mineral oil) in 55 ml of dry benzene a solution of 2.96 g of dimethyl [(2-oxo-3-fluoro-4-phenyl)-3Z-butenyl]phosphonate in 29 ml of dry benzene was added dropwise, with exclusion of moisture. Stirring was continued until the evolution of hydrogen had stopped; then at once a solution of 1α-[7'-(methoxycarbonyl)-hex-5'(Z)enyl]-2β-formyl-3α-hydroxy-5α-acetoxycyclopentane (3.40 g) in dry benzene (35 ml) was added.

The mixture was stirred for 1 hour at 25° C. then neutralized with acetic acid, and stirring was continued for 30 minutes. The organic phase was washed until neutral with water, dried, and the solvent was removed by evaporation. The crude product was purified by flash silica gel chromatography, using diethylether:ethyl alcohol mixture (98:2) as eluant, to give 4.25 g of pure 5Z,13E,16Z-9α,11α-dihydroxy-9-acetate-15-oxo-16-fluoro-18,19,20-trinor-17-phenylprosta-5,13,16-trienoic acid methyl ester as yellow oil, $[\alpha]_D = +400.8°$ (C=1, CHCl$_3$).

EXAMPLE 2

Under a nitrogen atmosphere, to a solution of 2 g of 1α-[7'-(methoxycarbonyl)-hex-5'(Z)enyl]-2β-formyl-5α-acetoxy-cyclopentane in 3,5 ml of distilled THF and 5,5 ml of water, 2.43 g of dimethyl[(2-oxo-3-fluoro-4-phenyl)-3Z-butenyl]phosphonate and 1.0 g of potassium hydrogen carbonate were added.

The solution was stirred at room temperature for 48 hours then was diluted with 50 ml of 2% acetic acid solution and extracted four times with 30 ml of diethyl ether, washed with water and dried over sodium sulfate. The solvent was removed and the crude was purified on silica gel using n-hexane:ethylacetate 3:1 as eluant to obtain 2.15 g of pure 5Z,13E,16Z-9α-hydroxy-9-acetate-15-oxo-16-fluoro-18,19,20-trinor-17-phenyl-prosta-5,13,16-trienoic acid methyl ester, $[\alpha]_D = +73.7°$, $[\alpha]_{365} = +148.5°$ (C−1, EtOH).

EXAMPLE 3

A solution of 1α-[7'-(methoxycarbonyl)-hexyl]-2β-formyl-3α-hydroxy-5α-acetoxy-cyclopentane (2.50 g) in 20 ml of dry benzene was added to a solution of 2-oxo-3-fluoro-4-phenyl-3Z-butylidene-triphenylphosphorane (4.8 g) in 40 ml of dry benzene.

The mixture was refluxed 2 hours under a nitrogen atmosphere then the solvent was removed in vacuo and the crude was purified on silica gel using ethylacetate:n-hexane 1:1 as eluant to give 3.25 g of pure 13E,16Z-9α,11α-dihydroxy-9-acetate-15-oxo-16-fluoro-18,19,20-trinor-17-phenyl-prosta-13,16-dienoic acid methyl ester, $[\alpha]_D = +51.7°$ (C−1, CHCl$_3$).

EXAMPLE 4

Into a stirred solution of NaBH$_4$ (0.21 g) in methanol (20.8 ml) cooled to −30° C. with external cooling-bath, a solution of 5Z,13E,16Z-9α,11α-dihydroxy-9-acetate-15-oxo-16-fluoro-18,19,20-trinor-17-phenyl-prosta-5,13,16-trienoic acid methyl ester (0.84 g) in methanol (10.4 ml) was dropped. The temperature was maintained between −25° and −30° C. for 10 minutes after addition was completed. The solution was then neutralized with acetic acid and the temperature was left to rise to room temperature.

The solution was diluted with 50 ml of ethyl acetate and washed with brine, dried and the solvent was removed by evaporation. The crude epimeric mixture of 5Z,13E,16Z-9α,11α-15(S,R)-trihydroxy-9-acetate-16-fluoro-18,19,20-trinor-17-phenyl-prosta-5,13,16-trienoic acid methyl ester was separated into the two 15S and 15R epimers by chromatographic purification on silica gel using ethyl acetate:n-hexane (9:1) as eluant to give 0.39 g of 5Z,13E,16Z-9α,11α-15S-trihydroxy-9-acetate-16-fluoro-18,19,20-trinor-17-phenyl-prosta-5,13,16-trienoic acid methyl ester, $[\alpha]_D = +34.7°$ (C=1, CHCl$_3$), and 0.41 g of 5Z,13E,16Z-9α,11α-15R-trihydroxy-9-acetate-16-fluoro-18,19,20-trinor-17-phenyl-prosta-5,13,16-trienoic acid methyl ester, $[\alpha]_D = +5.5°$ (C=1, CHCl$_3$).

EXAMPLE 5

In analogous fashion as described in Example 4, starting from 5Z,13E,16Z-9α-hydroxy-9-acetate-15-oxo-16-fluoro-18,19,20-trinor-17-phenyl-prosta-5,13,16-trienoic acid methyl ester (2 g), using the same reduction procedure and separating the mixture of epimeric alcohols into the two 15S and 15R epimers by preparative HPLC, there were obtained pure 5Z,13E,16Z,9α,15S-dihydroxy-9-acetate-16-fluoro-18,19,20-trinor-17-phenyl-prosta-5,13,16-trienoic acid methyl ester, less polar compound (0.9 g), $[\alpha]_D = +68.1°$, $[\alpha]_{365} = +228.6°$ (C=1, EtOH), and pure 5Z,13E,16Z,9α,15R-dihydroxy-9-acetate-16-fluoro-18,19,20-trinor-17-phenyl-prosta-5,13,16-trienoic acid methyl ester, more polar compound (1.1 g), $[\alpha]_D = +21.8°$, $[\alpha]_{365} = +27.0°$ (C−1, EtOH), NMR(CDCl$_3$) δp.p.m: 3.64 (3H, s); 4.79 (1H, d); 5.37 (2H, m); 5.82 (2H, m); 5.85 (1H, d); 7.2–7.6 (5H, m).

EXAMPLE 6

A stirred solution of 0.30 g of 5Z,13E,16Z-9α,11α-15R-trihydroxy-9-acetate-16-fluoro-18,19,20-trinor-17-phenyl-prosta-5,13,16-trienoic acid methyl ester in methanol (10 ml) was treated with a solution of 0.135 g of lithium hydroxide in water (1 ml).

The mixture was stirred at room temperature for 6 hours then neutralized to pH 6.2 with NaH$_2$PO$_4$ 10% aqueous solution, extracted with ethyl acetate, washed with brine and dried; the solvent was removed yielding 0.25 g of 5Z,13E,16Z-9α,11α-15R-trihydroxy-16-fluoro-18,19,20-trinor-17-phenylprosta-5,13,16-trienoic acid, $[\alpha]_D = -26°$ (C−1, ethanol).

According to the above described procedure, starting from 5Z,13E,16Z-9α,11α-15S-trihydroxy-9-acetate-16-fluoro-18,19,20-trinor-17-phenyl-prosta-5,13,16-trienoic acid methyl ester, the pure 5Z,13E,16Z-9α,11α-15S-trihydroxy-16-fluoro-18,19,20-trinor-17-phenyl-prosta- 5,13,16-trienoic acid was obtained, $[\alpha]_D = +27°$ (C=1, ethanol).

By analogous procedure the following compounds were prepared:

6Z,13E,16Z-9α,11α-15R-trihydroxy-16-fluoro-prosta-5,13,16-trienoic acid, $[\alpha]_D = -20.5°$;

5Z,13E,16Z-9α,11α-15R-trihydroxy-16-fluoro-20-methyl-prosta-5,13,16-trienoic acid, $[\alpha]_D = -21.7°$;

5Z,13E,16Z-9α,11α-15R-trihydroxy-16-fluoro-20-ethyl-prosta-5,13,16-trienoic acid, $[\alpha]_D = -21.3°$;

5Z,13E,16Z-9α,11α-15R-trihydroxy-16-fluoro-18,19,20-trinor-17-cyclohexyl-prosta-5,13,16-trienoic acid, $[\alpha]_D = -18°$;

5Z,13E,16Z-9α,11α-15R-trihydroxy-16-fluoro-18,19,20-trinor-17-(3'-chloro-phenyl)-prosta-5,13,16-trienoic acid, $[\alpha]_D = -26°$;

5Z,13E,16Z-9α,11α-15R-trihydroxy-16-fluoro-18,19,20-trinor-17-(4'-trifluoromethylphenyl)-prosta-5,13,16-trienoic acid, $[\alpha]_D = -24°$;

5Z,13E,16Z-9α,11α-15R-trihydroxy-16-fluoro-18,19,20-trinor-17-(2'-furyl)-prosta-5,13,16-trienoic acid, $[\alpha]_D = -20.9°$;

5Z,13E,16Z-9α,11α-15R-trihydroxy-16-fluoro-18,19,20-trinor-17-(2'-thienyl)-prosta-5,13,16-trienoic acid, $[\alpha]_D = -19.5°$;

5Z,13E,16Z-9α,11α-15R-trihydroxy-16-fluoro-18,19,20-trinor-17-(2'-pyrrolyl)-prosta-5,13,16-trienoic acid, $[\alpha]_D = -16°$;

5Z,13E,16Z-9α,11α-15R-trihydroxy-16-fluoro-18,19,20-trinor-17-(3'-pyridyl)-prosta-5,13,16-trienoic acid, $[\alpha]_D = -15.9°$;

5Z,13E,16Z-9α,11α-15R-trihydroxy-16-fluoro-18,19,20-trinor-17-(2'-pyrazinyl)-prosta-5,13,16-trienoic acid, $[\alpha]_D = -36°$; and 5Z,13E,16Z-9α,11α-15R-trihydroxy-16-fluoro-18,19,20-trinor-17-(3'-isoxazolyl)-prosta-5,13,16-trienoic acid, $[\alpha]_D = -17.6°$.

EXAMPLE 7

To a solution of 0.1 g of 5Z,13E,16Z,9α,15S-dihydroxy-9-acetate-16-fluoro-18,19,20-trinor-17-phenyl-prosta-5,13,16-trienoic acid methyl ester in 3 ml of dry methanol, 0.06 g of dry potassium carbonate were added under a nitrogen atmosphere. The solution was stirred for 24 hours at room temperature then quenched into 20 ml of ice and water and 5 ml of 30% sodium monophosphate.

The solution was extracted with diethyl ether dried and the solvent was removed to give a crude that was purified on silica gel chromatographic column using methylene chloride:ethanol 92:8 as mobile phase to afford 0.08 g of pure 5Z,13E,16Z,9α,15S-dihydroxy-16-fluoro-18,19,20-trinor-17-phenyl-prosta-5,13,16-trienoic acid methyl ester, $[\alpha]_D = +28°$ (C=1, EtOH).

EXAMPLE 8

Starting from the appropriate intermediate compounds obtained according to the procedure of the Examples 3 and 4, and proceeding according to the methods described in the Examples 6 and 7, the following prostadienoic acid derivatives and methyl esters were prepared:

13E,16Z-9α,11α,15R-trihydroxy-16-fluoro-18,19,20-trinor-17-phenyl-prosta-13,16-dienoic acid, $[\alpha]_D = -23.4°$;

13E,16Z-9α,11α,15S-trihydroxy-16-fluoro-18,19,20-trinor-17-phenyl-prosta-13,16-dienoic acd, $[\alpha]_D = +28.3$;

13E,16Z-9α,11α,15R-trihydroxy-16-fluoro-18,19,20-trinor-17-phenyl-prosta-13,16-dienoic acid methyl ester, $[\alpha]_D = -22.9°$;

13E,16Z-9α,11α,15S-trihydroxy-16-fluoro-18,19,20-trinor-17-phenyl-prosta-13,16-dienoic acid methyl ester, $[\alpha]_D = +28.0°$;

13E,16Z-9α,11α,15R-trihydroxy-16fluoro-prosta-13,16-dienoic acid, $[\alpha]_D = -19.8°$; and 13E,16Z-9α,11α,15R-trihydroxy-16-fluoro-prosta-13,16-dienoic acid methyl ester, $[\alpha]_D = -20.0$.

EXAMPLE 9

Using the procedure described in Example 1, under a nitrogen atmosphere, to a suspension of 80% NaH (dispersion in mineral oil) (0.60 g) in dry benzene (112 ml), with stirring, a solution of 5.90 g of dimethyl [(2-oxo-3-fluoro-4-cyclohexyl)-3Z-butenyl]phosphonate in 50 ml of dry benzene was added. Stirring was continued for 30 minutes, then a solution of 6.8 g of 1α-[7'-(methoxycarbonyl)hexyl]-2β-formyl-3α-hydroxy-5α-acetoxycyclopentane in 50 ml of dry benzene was added. The mixture was stirred for 1 hour at 25° C. then neutralized with acetic acid and stirring was continued for 30 minutes.

The organic phase was washed until neutral with water, dried and the solvent was removed by evaporation. After purification on a silica gel column, 8.55 g of pure 13E,16Z-9α,11α-dihydroxy-9-acetate-15-oxo-16-fluoro-18,19,20-trinor-17-cyclohexyl-prosta-13,16-dienoic acid methyl ester was obtained as oil, $[\alpha]_D = +48.7°$ (C=1, CHCl$_3$).

Reduction of this compound according to the procedure of Example 4 and removal of the 9-acetate group according to the procedure of Example 7 led to 13E,16Z-9α,11α-15R-trihydroxy-16-fluoro-18,19,20-trinor-17-cyclohexyl-prosta-13,16-dienoic acid methyl ester, mass spectrum M/e: 426, 408, 395, 390; 13E,16Z-9α,11α-15S-trihydroxy-16-fluoro-18,19,20-trinor-17-cyclohexyl-prosta-13,16-dienoic acid methyl ester, mass spectrum M/e: 426, 408, 395, 390.

EXAMPLE 10

A 0.1N solution of CH$_3$MgI in diethyl ether was added dropwise into a solution of 5Z,13E,16Z-9α,11α-dihydroxy-15-oxo-16-fluoro-18,19,20-trinor-17-(2'-thienyl)-prosta-5,13,16-trienoic acid-1-trimethylsilyl ester-9,11-bis-trimethylsilylether (0.72 g) in 10 ml of dry diethyl ether.

The reaction mixture was stirred for 1 hour then quenched with aqueous acetic acid, then washed with saturated ammonium chloride solution, extracted with diethyl ether, washed with water and the organic phase was dried and evaporated to dryness.

The crude mixture of 15-epimeric alcohols was separated by silica gel chromatography yielding 0.15 g of pure 5Z,13E,16Z-9α,11α,15R-trihydroxy-15-methyl-16-fluoro-18,19,20-trinor-17-(2'-thienyl)-prosta-5,13,16-trienoic acid, mass spectrum (trimethylsilyl derivative) M/e: 712, 623, 534,, 445, and 0.14 g of pure 5Z,13E,16Z-9α,11α-15S-trihydroxy-15-methyl-16-fluoro-18,19,20-trinor-17-(2'-thienyl)-prosta-5,13,16-trienoic acid, mass spectrum (trimethylsilyl derivative) M/e: 712, 623, 534, 445.

Using the same method the following derivatives were prepared:

5Z,13E,16Z-9α,11α-15R-trihydroxy-15-methyl-16-fluoro-18,19,20-trinor-17-(2'-furyl)-prosta-5,13,16-trienoic acid;

5Z,16Z-9α,11α-15R-trihydroxy-15-methyl-16-fluoro-18,19,20-trinor-17-(2′-furyl)-prosta-5,16-dien-13-ynoic acid;

5Z,13E,16Z-9α,11α-15R-trihydroxy-15-methyl-16-fluoro-18,19,20-trinor-17-(3′-thienyl)-prota-5,13,16-trienoic acid;

5Z,16Z-9α,11α-15R-trihydroxy-15-methyl-16-fluoro-18,19,20-trinor-17-(2′-thienyl)-prosta-5,16-dien-13-ynoic acid;

5Z,13E,16Z-9α,11α-15R-trihydroxy-15-methyl-16-fluoro-prosta-5,13,16-trienoic acid;

5Z,16Z-9α,11α-15R-trihydroxy-15-methyl-16-fluoro-prosta-5,16-dien-13-ynoic acid;

5Z,13E,16Z-9α,11α-15R-trihydroxy-15-methyl-16-fluoro-18,19,20-trinor-17-cyclohexyl-prosta-5,13,16-trienoic acid;

5Z,16Z-9α,11α-15R-trihydroxy-15-methyl-16-fluoro-18,19,20-trinor-17-cyclohexyl-prosta-5,16-dien-13-ynoic acid;

5Z,13E,16Z-9α,11α-15R-trihydroxy-15-methyl-16-fluoro-18,19,20-trinor-17-phenyl-prosta-5,13,16-trienoic acid;

5Z,16Z-9α,11α-15R-trihydroxy-15-methyl-16-fluoro-18,19,20-trinor-17-phenyl-prosta-5,16-dien-13-ynoic acid; and the corresponding 15S epimers.

EXAMPLE 11

A solution of 5Z,13E,16Z-9α,11α-15S-trihydroxy-14-bromo-16-fluoro-17-(3′-pyridyl)-prosta-5,13,16-trienoic acid (0.62 g) in ethanol (15 ml) was treated with a 0.1N solution of sodium ethoxide in ethanol (15 ml). The mixture was stirred for 30 minutes then neutralized with acetic acid; the solvent was removed and the residue, dissolved in 50 ml of ethyl acetate, was washed with saturated sodium sulfate solution, dried and evaporated at reduced pressure.

The crude oily residue was purified through silica gel chromatography using methylene chloride; methanol (95:5) to give pure 5Z,16Z-9α,11α-15R-trihydroxy-16-fluoro-17-(3′-pyridyl)-prosta-5,16-dien-13-ynoic acid (0.48 g), $[\alpha]_D = -7.6°$ (C=1,EtOH).

By proceeding analogously the following compounds were obtained:

5Z,16Z-9α,11α-15R-trihydroxy-16-fluoro-prosta-5,16-dien-13-ynoic acid, $[\alpha]_D = -19.7°$;

5Z,16Z-9α,11α-15R-trihydroxy-16-fluoro-20-methyl-prosta-5,16-dien-13-ynoic acid, $[\alpha]_D = -21.0°$;

5Z,16Z-9α,11α-15R-trihydroxy-16-fluoro-20-ethyl-prosta-5,16-dien-13-ynoic acid, $[\alpha]_D = -21.9°$;

5Z,16Z-9α,11α-15R-trihydroxy-16-fluoro-18,19,20-trinor-17-cyclohexyl-prosta-5,16-dien-13-ynoic acid, $[\alpha]_D = -18.5°$;

5Z,16Z-9α,11α-15R-trihydroxy-16-fluoro-18,19,20-trinor-17-phenyl-prosta-5,16-dien-13-ynoic acid, $[\alpha]_D = -31.5°$;

5Z,16Z-9α,11α-15R-trihydroxy-16-fluoro-18,19,20-trinor-17-(2′-furyl)-prosta-5,16-dien-13-ynoic, acid $[\alpha]_D = -37.2°$;

5Z,16Z-9α,11α-15R-trihydroxy-16-fluoro-18,19,20-trinor-17-(2′-thienyl)-prosta-5,16-dien-13-ynoic acid, $[\alpha]_D = -31.5°$;

5Z,16Z-9α,11α-15R-trihydroxy-16-fluoro-18,19,20-trinor-17-(2′-pyrrolyl)-prosta-5,16-dien-13-ynoic acid, $[\alpha]_D = -16.5°$;

5Z,16Z-9α,11α-15R-trihydroxy-16-fluoro-18,19,20-trinor-17-(2′-pyridyl)-prosta-5,16-dien-13-ynoic acid, $[\alpha]_D = -51.2°$;

5Z,16Z-9α,11α-15R-trihydroxy-16-fluoro-18,19,20-trinor-17-(2′-pyrazinyl)-prosta-5,16-dien-13-ynoic acid, $[\alpha]_D = -36.0°$;

5Z,16Z-9α,11α-15R-trihydroxy-16-fluoro-18,19,20-trinor-17-(3′-isoxazolyl)-prosta-5,16-dien-13-ynoic acid, $[\alpha]_D = -17.3°$;

5Z,16Z-9-oxo-11α-15R-dihydroxy-16-fluoro-prosta-5,16-dien-13-ynoic acid, $[\alpha]_D = -79.0°$;

5Z,16Z-9-oxo-11α-15R-dihydroxy-16-fluoro-20-methyl-prosta-5,16-dien-13-ynoic acid, $[\alpha]_D = -69.8$;

5Z,16Z-9-oxo-11α-15R-dihydroxy-16-fluoro-20-ethyl-prosta-5,16-dien-13-ynoic acid, $[\alpha]_D = -73.5°$;

5Z,16Z-9-oxo-11α-15R-dihydroxy-16-fluoro-18,19,20-trinor-17-cyclohexyl-prosta-5,16-dien-13-ynoic acid, $[\alpha]_D = -81.0°$;

5Z,16Z-9-oxo-11α-15R-dihydroxy-16-fluoro-18,19,20-trinor-17-phenyl-prosta-5,16-dien-13-ynoic acid, $[\alpha]_D = -72°$;

5Z,16Z-9-oxo-11α-15R-dihydroxy-16-fluoro-18,19,20-trinor-17-(2′-furyl)prosta-5,16-dien-13-ynoic acid, $[\alpha]_D = -58.6°$;

5Z,16Z-9-oxo-11α-15R-dihydroxy-16-fluoro-18,19,20-trinor-17-(2′-thienyl)-prosta-5,16-dien-13-ynoic acid, $[\alpha]_D = -47.5°$;

5Z,16Z-9-oxo-11α-15R-dihydroxy-16-fluoro-18,19,20-trinor-17-(2′-pyrrolyl)-prosta-5,16-dien-13-ynoic acid, $[\alpha]_D = -61.7°$;

5Z,16Z-9-oxo-11α-15R-dihydroxy-16-fluoro-18,19,20-trinor-17-(3′-pyridyl)-prosta-5,16-dien-13-ynoic acid, $[\alpha]_D = -87.3°$;

5Z,16Z-9-oxo-11α-15R-dihydroxy-16-fluoro-18,19,20-trinor-17-(2′-pyrazinyl)-prosta-5,16-dien-13-ynoic acid, $[\alpha]_D = -42.9°$;

5Z,16Z-9-oxo-11α-15R-dihydroxy-16-fluoro-18,19,20-trinor-17-(3′-isoxazolyl)-prosta-5,16-dien-13-ynoic acid, $[\alpha]_D = -31.2°$.

EXAMPLE 12

(a) To a solution of 0.530 g of 5Z,13E,16Z-9α,11α,15R-trihydroxy-9-acetate-16-fluoro-18,19,20-trinor-17-phenyl-prosta-5,13,16-trienoic acid methyl ester in 10 ml of dry CH₂Cl₂, 0.252 ml of DHP and a catalytic amount of p-toluenesulfonic acid (about 0.003 g) were added.

The solution was stirred at room temperature for 2 hours; then it was extracted with diethyl ether (50 ml) and washed twice with NaHCO₃ 5% solution, twice with water and then dried. The solvent was removed in vacuum and the crude (0.680 g) was dissolved in 10 ml of dry methanol and 0.191 g of K₂CO₃ were added.

The solution was stirred at room temperature for 6 hours then was treated with 30% aqueous solution of NaH₂PO₄ (50 ml) and extracted with 4 portions of 30 ml of ethyl acetate. The organic phase was washed, dried and the solvent was distilled in vacuum. The residue was purified using a flash chromatography on silica gel and ethyl acetate: n-hexane (40:60) as eluant so obtaining 0.496 g of pure 5Z,13E,16Z-9α,11α-15R-trihydroxy-18,19,20-trinor-16-fluoro-17-phenyl-prosta-5,13,16-trienoic acid methyl ester 11,15-bis THP ether.

(b) A solution of 0.86 g of 5Z,13E,16Z-9α,11α,15R-trihydroxy-9-acetate-16-fluoro-18,19,20-trinor-17-phenyl-prosta-5,13,16-trienoic acid methyl ester-11,15-bis-THP ether in methanol (15 ml) was reacted at room temperature for 3 hours with a solution of 0.3 g of lithium hydroxide in water (3 ml). The mixture was treated with NaH₂PO₄ 10% aqueous solution until pH 6.2, then extracted with ethyl acetate, washed with water and dried over Na$_2$SO$_4$. P The solvent was removed to give 0.75 g of 5Z,13E,16Z-9α,11α,15R-trihydroxy-16-fluoro-18,19,20-trinor-17-phenyl-prosta-5,13,16-trienoic acid-11,15-bis-THP ether.

In analogous fashion, starting from the appropriate intermediate compounds prepared according to the procedure described in example 4, the 11,15-bis-THP ethers of the compounds mentioned in the examples 5 and 8 were obtained.

EXAMPLE 13

Into a solution of 0.450 g of 5Z,13E-9α-15R-dihydroxy-9-acetate-18,19,20-trinor-16-fluoro-17-(2'-furyl)-prosta-5,13,16-trienoic acid methyl ester in 3 ml of dry DMF, 0.070 g of imidazole and 0.147 g of tert-butyl-dimethyl-chloro silane were added.

The solution was stirred for 6 hours at room temperature then was quenched with 40 ml of iced water and extracted three times with diethyl ether (30 ml). The organic phase was washed with water, dried and the solvent was distilled at reduced pressure.

The crude was purified with silica gel flash chromatography using ethyl acetate: n-hexane (20:80) as eluant and 0.506 g of pure 5Z,13E-9α-15R-dihydroxy-9-acetate-18,19,20-trinor-16-fluoro-17-(2'-furyl)-prosta-5,13,16-trienoic acid methyl ester-15-tert-butyl-dimethyl silyl ether were obtained.

The product (0.400 g) was dissolved in 5 ml of dry methanol and 0.075 g of K$_2$CO$_3$ were added; the reaction mixture was stirred for 8 hours, quenched with 40 ml of 30% aqueous NaH$_2$PO$_4$, extracted with ethyl acetate, dried and evaporated to dryness to give 0.452 g of 5Z,13E-9α-15R-dihydroxy-18,19,20-trinor-16-fluoro-17-(2'-furyl)-prosta-5,13,16-trienoic acid methyl ester-15-tert-butyl-dimethyl silyl ether. The product was dissolved in 10 ml of dry benzene and 1 ml of DMSO, then 0.161 g of dicyclohexylcarbodiimide and 0.1 ml of 0.1M solution of pyridinium trifluoroacetate were added.

The solution was stirred 1 hour at room temperature then 6 ml of 30% aqueous NaH$_2$PO$_4$ solution were added. The solid was filtered and washed with benzene; the organic phase was washed with water, dried and the solvent was removed to obtain the crude 9-oxo-5Z,13E-15R-hydroxy-18,19,20-trinor-16-fluoro-17-(2'-furyl)-prosta-5,13,16-trienoic acid methyl ester-15-tert-butyl-dimethyl silyl ether (0.450 g). To the solution of the crude product in 15 ml of THF were added 0.220 g of acetic acid and 0.320 g of tetrabutylammoniumfluoride and the mixture was stirred 8 hours at room temperature. The reaction mixture was diluted with 50 ml of ethyl acetate, washed with 5% NaHCO$_3$, and with water, then it was dried and the solvent was removed. The crude product was purified by silica gel chromatography using ethyl acetate: n-hexane (70:30) as eluant, so obtaining 0.215 g of pure 5Z,13E-9-oxo-15R-hydroxy-18,19,20-trinor-16-fluoro-17-(2'-furyl)-prosta-5,13,16-trienoic acid methyl ester, $[\alpha]_D = -27.4°$ (C=1, EtOH).

By analogous procedure starting from the suitable prostatrienoic acid derivatives, the following compounds were prepared:

5Z,13E,16Z-9-oxo-15R-hydroxy-16-fluoro-18,19,20-trinor-17-phenyl-prosta-5,13,16-trienoic acid methyl ester, $[\alpha]_D = -81.4°$, $[\alpha]_{365} = -492°$ (C=1, EtOH), NMR (CDCl$_3$), δp.p.m: 3.64 (3H, s); 4.79 (1H, dt); 5.37 (2H, m); 5.82 (1H, d); 7.2–7.6 (5H, m);

5Z,13E,16Z-9-oxo-15S-hydroxy-16-fluoro-18,19,20-trinor-17-phenyl-prosta-5,13,16-trienoic acid methyl ester, $[\alpha]_D = -40°$, $[\alpha]_{365} = -289.5°$ (C=1, EtOH);

5Z,13E,16Z-9-oxo-15R-hydroxy-16-fluoro-18,19,20-trinor-17-(2'-pyridyl)-prosta-5,13,16-trienoic acid methyl ester, $[\alpha]_D = -79.5°$;

5Z,13E,16Z-9-oxo-15S-hydroxy-16-fluoro-18,19,20-trinor-17-(2'-pyridyl)-prosta-5,13,16-trienoic acid methyl ester, $[\alpha]_D = -43.2°$;

5Z,13E,16Z-9-oxo-15R-hydroxy-16-fluoro-prosta-5,13,16-trienoic acid methyl ester, $[\alpha]_D = -41.2°$.

Furthermore, by analogous way, the product obtained in Example 12(a) was first oxidized and then de-protected at the 11 and 15 positions to give 5Z,13E,16Z-9-oxo-11α,15R-dihydroxy-16-fluoro-18,19,20-trinor-17-phenyl-prosta-5,13,16-trienoic acid methyl ester, $[\alpha]_D = -93.3°$, $[\alpha]_{365} = -52.4°$.

EXAMPLE 14

By proceeding in analogous way as reported in Example 13, the below listed prostadienoic acids and methyl esters were prepared:

13E,16Z-9-oxo-11α,15R-dihydroxy-16-fluoro-18,19,20-trinor-17-phenyl-prosta-13,16-dienoic acid $[\alpha]_D = -88.7°$;

13E,16Z-9-oxo-11α,15S-dihydroxy-16-18,19,20-trinor-17-phenyl-prosta-13,16-dienoic acid, $[\alpha]_D = -47.5°$;

13E,16Z-9-oxo-11α,15R-dihydroxy-16-fluoro-18,19,20-trinor-17-phenyl-prosta-13,16-dienoic acid methyl ester, $[\alpha]_D = -91.2°$;

13E,16Z-9-oxo-11α,15S-dihydroxy-16-fluoro-18,19,20-trinor-17-phenyl-prosta-13,16-dienoic acid methyl ester, $[\alpha]_D = -48.1°$;

13E,16Z-9-oxo-11α,15R-dihydroxy-16-fluoro-prosta-13,16-dienoic acid, $[\alpha]_D = -77.5°$;

13E,16Z-9-oxo-11α,15R-dihydroxy-16-fluoro-prosta-13,16-dienoic acid methyl ester, $[\alpha]_D = -78.7°$;

13E,16Z-9-oxo-15R-hydroxy-16-fluoro-18,19,20-trinor-17-phenyl-prosta-13,16-dienoic acid, $[\alpha]_D = -82.5°$;

13E,16Z-9-oxo-15R-hydroxy-16-fluoro-18,19,20-trinor-17-phenyl-prosta-13,16-dienoic acid methyl ester, $[\alpha]_D = -85.5°$;

13E,16Z-9-oxo-15S-hydroxy-16-fluoro-18,19,20-trinor-17-phenyl-prosta-13,16-dienoic acid methyl ester, $[\alpha]_D = -48.2°$;

13E,16Z-9-oxo-15R-hydroxy-16-fluoro-prosta-13,16-dienoic acid methyl ester, $[\alpha]_D = -67.8°$;

13E,16Z-9-oxo-15R-hydroxy-16-fluoro-prosta-13,16-dienoic acid, $[\alpha]_D = -68.2°$.

EXAMPLE 15

To a suspension of 0.661 g of NaH (80% dispersion in mineral oil) in 92 ml of benzene a solution of 4.6 g of dimethyl[(2-oxo-3-fluoro)hept-3-Z-enyl]phosphonate in 40 ml of dry benzene was added dropwise, and stirring was continued for an hour.

A gelatinous suspension was formed to which a solution of 5.58 g of 1α-[(2β-formyl-3α,5α-dihydroxy-3-benzoate)-cyclopent-1-yl]-acetic acid-γ-lactone in 70 ml of dry benzene was added at once. The mixture was stirred for 20 minutes and then diluted with 60 ml of 6% (W/V) aqueous NaH$_2$PO$_4$ and the organic phase was separated, washed until neutral with brine, dried and the solvent was removed by evaporation. The crude product (9.8 g) was crystallized twice dissolving it in hot methanol: the white crystals filtered by suction were collected to yield 6.25 g of pure 1α-{[2β-(3'-oxo- 4'-fluoro-octa-1'(E),4'(Z)-dienyl)-3α,5α-dihydroxy-3-benzoate]-cyclopent-1-yl}-acetic acid-γ-lactone, mp. 133°–135° C., [α]$_D$=−95° (C=1, CHCl$_3$).

EXAMPLE 16

A stirred suspension of 0.104 g of NaH(80% dispersion in mineral oil) in 30 ml of dry benzene was reacted with a solution of 1.06 g of dimethyl[(2-oxo-3-fluoro-4-phenyl)-but-3Z-enyl]phosphonate in 10 ml of dry benzene and stirred for an hour.

A gelatinous suspension was formed to which 0.61 g of finely divided N-bromo-succinimide was added at once. After 15 minutes of stirring a solution of 0.82 g of 1α-[(2β-formyl-3α,5α-dihydroxy-3-benzoate)-cyclopent-1-yl]-acetic acid-γ-lactone in 20 ml of dry benzene was added.

The mixture was stirred for 20 minutes and then was diluted with 20 ml of 6% (W/V) aqueous NaH$_2$PO$_4$. The organic phase was separated, washed until neutral, dried and the solvent removed by evaporation.

After purification on a silica gel column 0.97 g of 1α{[2β-(2'-bromo-3'-oxo-4'-fluoro-5'-phenyl-1'(E)),4'(Z)-pentadienyl)-3α,5α-dihydroxy-3-benzoate]-cyclopent-1α-yl}acetic acid-γ-lactone, was obtained as oil, [α]$_D$=−98° (C=1, CHCl$_3$).

EXAMPLE 17

A solution of 1α{[2β-(2'-bromo-3'-oxo-4'-fluoro-5'-phenyl-1'(E),4'(Z)-pentadienyl)-3α,5α-dihydroxy-3-benzoate]-cyclopent-1α-yl}acetic acid-γ-lactone (3.09 g) in ethylene glycol dimethyl ether (50 ml) was dropped into a cooled solution (−25° C.) of NaBH$_4$ (0.585 g) in methanol (70 ml). During the addition the temperature was maintained between −20° C. and −25° C. with external cooling bath of dry ice and acetone.

In an hour the reaction was completed and the reaction mixture was quenched adding 1.5 ml of acetic acid, then the temperature was left to rise to the room temperature and the methanol was evaporated. The solution was diluted with 20 ml of water and was extracted twice with 50 ml of ethyl acetate. The organic phase was washed with water and dried; the crude mixture of the epimeric alcohols was separated using HPLC apparatus and a preparative silica column in one step isocratic separation using ethyl acetate: ciclohexane mixture (40:60) as eluant.

A less polar compound (1.130 g) corresponding to 1α{[2β-(2'-bromo-3'(S)-hydroxy-4'-fluoro-5'-phenyl-1'(E),4'(Z)-pentadienyl)-3α, 5α-dihydroxy-3-benzoate]-cyclopent-1α-yl}acetic acid-γ-lactone, [α]$_D$=−79.6° (C=1, CHCl$_3$), and a more polar compound (1.600 g) corresponding to 1α{[2β-(2'-bromo-3'(R)-hydroxy-4'-fluoro-5'-phenyl-1'(E),4'(Z)-pentadienyl)-3α,5α-dihydroxy-3-benzoate]-cyclopent-1α-yl}-acetic acid-γ-lactone, [α]$_D$=−69.5° (C=1, CHCl$_3$), were obtained.

EXAMPLE 18

To a solution of 1.920 g of 1α{[2β-(2'-bromo-3'(S)-hydroxy-4'-fluoro-5'phenyl-1'(E),4(Z)-pentadienyl)-3α,5α-dihydroxy-3-benzoate]-cyclopent-1α-yl}acetic acid-γ-lactone in 30 ml of methanol was added 0.262 g of K$_2$CO$_3$. The mixture was stirred for 3 hours then was diluted with 40 ml of 30% NaH$_2$PO$_4$ solution and extracted three times with 50 ml of ethylacetate. The organic phase was washed with water, dried and the solvent was removed; the crude 1α{[2β-(2'-bromo-3'(S)-hydroxy-4'-fluoro-5'-phenyl-1'(E),4'(Z)-pentadienyl)-3α,5α-dihydroxy]-cyclopent-1α-yl}acetic acid-γ-lactone (1.25 g) was dissolved in 10 ml of dry CH$_2$Cl$_2$ and 0.856 ml of dihydropyran and a catalytic amount of p-toluene sulphonic acid (about 0.006 g) were added.

The solution was stirred at room temperature for about half an hour and a deep blue coloured mixture was obtained; the solution was extracted with 50 ml of ethyl acetate, washed with brine, dried and the solvent was removed. The crude residue was chromatographed on silica gel and eluted with cyclohexane: ethyl acetate mixture (70:30) to give 0.650 g of pure 1α{[2β-(2'-bromo-3'(S)-hydroxy-4'-fluoro-5'-phenyl-1'(E),4'(Z)-pentadienyl)-3α,5α-dihydroxy]-3,3'-bis-tetrahydropyranyl ether-cyclopent-1α-yl}acetic acid-γ-lactone.

EXAMPLE 19

Under nitrogen atmosphere a 20% solution of DIBA in toluene (2.49 ml) was added over a 15 minutes period to a stirred solution of 1α[2β-(2'-bromo-3'(S)-hydroxy-4'-fluoro-5'-phenyl-1'(E),4'(Z)-pentadienyl)-3α,5α-dihydroxy-3,3'-bistetrahydropyranyl ether]-cyclopent-1α-yl}acetic acid-γ-lactone (1.120 g) in 10 ml of dry toluene, cooled to −70° C. Stirring was continued for 30 minutes then the reaction mixture was treated with 2N-isopropanol in toluene, and after 10 minutes, warmed to 0°–2° C. and treated with 1.5 ml of water, 2 g of anhydrous sodium sulfate and 2.5 g of celite ®, then filtered.

The filtrate was evaporated to dryness under vacuum to give 1.050 g of 1α{[2β-(2'-bromo-3'(S)-hydroxy-4'-fluoro-5'-phenyl-1'(E),4'(Z)-pentadienyl)-3α,5α-dihydroxy-3,3'-bis-tetrahydropyranyl ether]-cyclopent-1α-yl}acetaldehyde-γ-hemiacetal.

EXAMPLE 20

Under argon atmosphere, to a solution of 1.903 g of triphenyl(4-carboxybutyl)-phosphonium bromide in 7.5 ml of dry DMSO, 0.965 g of potassium-ter-butoxide were added portionwise. The stirring was continued until a purple solution of the ylide was obtained, then 0.750 g of 1α{[2β-(2'-bromo-3'(S)hydroxy-4'-fluoro-5'-phenyl-1'(E),4'(Z)-pentadienyl)-3α,5α-dihydroxy-3,3'-bis-tetrahydropyranyl ether]-cyclopent-1α-yl}acetaldehyde-γ-hemiacetal dissolved in 7.5 ml of dry DMSO, were added.

The reaction mixture was stirred for 3 hours at room temperature, then placed in an ice bath and diluted with 70 ml of iced water. The alkaline aqueous phase was extracted with diethyl ether and the etheral extracts were backwashed with 1N NaOH and then discarded. The aqueous alkaline phases were combined, acidified to pH 5 and extracted with diethyl ether: n-pentane (1:1) to give 0.67 g of 5Z,16Z-9α,11α-15R-trihydroxy-16-fluoro-18,19,20-trinor-17-phenyl-prosta-5,16-dien-13-ynoic acid-11,15-bis-THP ether.

EXAMPLE 21

A solution of the crude product obtained in Example 20 (0.67 g) in acetone (15 ml) was treated for 8 hours at 35° C. with an aqueous 0.2N solution of oxalic acid (16 ml). After the removal of the acetone in vacuo the aqueous phase was extracted with diethyl ether and the combined etheral extracts were washed until neutral with water, dried, and evaporated to dryness.

The residue was chromatographed on silica gel with methylene chloride:ethyl acetate (80:20) as eluant to give 0.340 g of pure 5Z,16Z-9α,11α-15R-trihydroxy-16- fluoro-18,19,20-trinor-17-phenyl-prosta-5,16-dien-13-ynoic acid, $[\alpha]_D = -31.5°$ (C=1, EtOH); mass spectrum (trimethylsilyl derivative) M/e: 690, 601, 512, 423.

Following the procedure described in the preceding Examples 17 to 20 and in this Example 21, the compound obtained in Example 15 was converted into 5Z,13E,16Z-9α,11α,15R-trihydroxy-16-fluoro-prosta-5,13,16-trienoic acid.

In analogous fashion the following compounds were prepared:

5Z,16Z-9α,11α-15R-trihydroxy-16-fluoro-prosta-5,16-dien-13-ynoic acid, $[\alpha]_D = -19.7°$;

5Z,16Z-9α,11α,15R-trihydroxy-16-fluoro-20-methyl-prosta-5,16-dien-13-ynoic acid, $[\alpha]_D = -21.0°$;

5Z,16Z-9α,11α,15R-trihydroxy-16-fluoro-20-ethyl-prosta-5,16-dien-13-ynoic acid, $[\alpha]_D = -21.9°$;

5Z,16Z-9α,11α,15R-trihydroxy-16-fluoro-18,19,20-trinor-17-cyclohexyl-prosta-5,16-dien-13-ynoic acid, $[\alpha]_D = -18.5°$;

5Z,16Z-9α,11α,15R-trihydroxy-16-fluoro-18,19,20-trinor-17-(2'-furyl)-prosta-5,16-dien-13-ynoic acid, $[\alpha]_D = -37.2°$;

5Z,16Z-9α,11α,15R-trihydroxy-16-fluoro-18,19,20-trinor-17-(2'-thienyl)-prosta-5,16-dien-13-ynoic acid, $[\alpha]_D = -31.5°$;

5Z,16Z-9α,11α,15R-trihydroxy-16-fluoro-18,19,20-trinor-17-(2'-pyrrolyl)-prosta-5,16-dien-13-ynoic acid, $[\alpha]_D = -16.5°$;

5Z,16Z-9α,11α,15R-trihydroxy-16-fluoro-18,19,20-trinor-17-(3'-pyridyl)-prosta-5,16-dien-13-ynoic acid, $[\alpha]_D = -7.6°$;

5Z,16Z-9α,11α,15R-trihydroxy-16-fluoro-18,19,20-trinor-17-(2'-pyrazinyl)-prosta-5,16-dien-13-ynoic acid, $[\alpha]_D = -36.0°$; and 5Z,16Z-9α,11α,15R-trihydroxy-16-fluoro-18,19,20-trinor-17-(3'-isoxazolyl)-prosta-5,16-dien-13-ynoic acid, $[\alpha]_D = -17.3°$.

EXAMPLE 22

A solution of 0.42 g of 5Z,16Z-9α,11α-15R-trihydroxy-16-fluoro-18,19,20-trinor-17-phenyl-prosta-5,16-dien-13-ynoic acid-11,15-bis-THP ether in 20 ml of acetone was cooled to −15° C. and then treated with 0.8 ml of Jone's reagent, added over 4 minutes. The reaction mixture was allowed to warm up to −10° C. and kept for 20 minutes at that temperature. After dilution with benzene (108 ml) the organic phase was repeatedly washed with saturated ammonium sulphate solution until neutral, dried and evaporated to dryness, yielding 0.40 g of 5Z,16Z-9-oxo-11α-15R-dihydroxy-16-fluoro-18,19,20-trinor-17 phenyl-prosta-5,16-dien-13-ynoic acid-11,15-bis-THP ether. A solution of the crude product was deacetalated by treatment with aqueous 0.2N solution of oxalic acid according to the procedure described in Example 21.

The crude 5Z,16Z-9-oxo-11α-15R-dihydroxy-16-fluoro-18,19,20 trinor-17-phenyl-prosta-5,16-dien-13-ynoic acid was chromatographed on silica gel with methylene chloride:ethyl acetate (90:10) as eluant to give 0.185 g of pure 5Z,16Z-9-oxo-11α-15R-dihydroxy-16-fluoro-18,19,20-trinor-17-phenyl-prosta-5,16-dien-13-ynoic acid, $[\alpha]_D = -72°$ (C=1, EtOH).

Using analogous procedure as that described above the following compounds were obtained:

5Z,16Z-9-oxo-11α-15R-dihydroxy-16-fluoro-prosta-5,16-dien-13-ynoic acid, $[\alpha]_D = -79°$;

5Z,16Z-9-oxo-11α-15R-dihydroxy-16-fluoro-20-methyl-prosta-5,16-dien-13-ynoic acid, $[\alpha]_D = -69.8°$;

5Z,16Z-9-oxo-11α-15R-dihydroxy-16-fluoro-20-ethyl-prosta-5,16-dien-13-ynoic acid, $[\alpha]_D = -73.5$;

5Z,16Z-9-oxo-11α-15R-dihydroxy-16-fluoro-18,19,20-trinor-17-cyclohexyl-prosta-5,16-dien-13-ynoic acid, $[\alpha]_D = -81°$;

5Z,16Z-9-oxo-11α-15R-dihydroxy-16-fluoro-18,19,20-trinor-17-(2'-furyl)-prosta-5,16-dien-13-ynoic acid, $[\alpha]_D = -58.6°$;

5Z,16Z-9-oxo-11α-15R-dihydroxy-16-fluoro-18,19,20-trinor-17-(2'-thienyl)-prosta-5,16-dien-13-ynoic acid, $[\alpha]_D = -47.5°$;

5Z,16Z-9-oxo-11α-15R-dihydroxy-16-fluoro-18,19,20-trinor-17-(2'-pyrrolyl)-prosta-5,16-dien-13-ynoic acid, $[\alpha]_D = -61.7°$;

5Z,16Z-9-oxo-11α-15R-dihydroxy-16-fluoro-18,19,20-trinor-17-(3'-pyridyl)-prosta-5,16-dien-13-ynoic acid, $[\alpha]_D = -87.3°$;

5Z,16Z-9-oxo-11α-15R-dihydroxy-16-fluoro-18,19,20-trinor-17-(2'-pyrazinyl)-prosta-5,16-dien-13-ynoic acid, $[\alpha]_D = -42.9°$; and 15Z,16Z-9-oxo-11α-15R-dihydroxy-16-fluoro-18,19,20-trinor-17-(3'-isoxazolyl)-prosta-5,16-dien-13-ynoic acid, $[\alpha]_D = -31.2°$.

In analogous fashion, starting from the suitable 11,15-bis-THP-ether derivatives prepared according to the procedure described in example 12(b), the following compounds were obtained too:

5Z,13E,16Z-9-oxo-11α,15R-dihydroxy-16-fluoro-prosta-5,13,16-trienoic acid, $[\alpha]_D = -81.5°$;

5Z,13E,16Z-9-oxo-11α-15R-dihydroxy-16-fluoro-20-methyl-prosta-5,13,16-trienoic acid, $[\alpha]_D = -71.2°$;

5Z,13E,16Z-9-oxo-11α-15R-dihydroxy-16-fluoro-20-ethyl-prosta-5,13,16-trienoic acid, $[\alpha]_D = -72.0°$;

5Z,13E,16Z-9-oxo-11α-15R-dihydroxy-16-fluoro-18,19,20-trinor-17-cyclohexyl-prosta-5,13,16-trienoic acid, $[\alpha]_D = -82.5°$;

5Z,13E,16Z-9-oxo-11α-15R-dihydroxy-16-fluoro-18,19,20-trinor-17-(3'-chloro-phenyl)-prosta-5,13,16-trienoic acid, $[\alpha]_D = -87°$;

5Z,13E,16Z-9-oxo-11α-15R-dihydroxy-16-fluoro-18,19,20-trinor-17-(4'-trifluoromethylphenyl)-prosta-5,13,16-trienoic acid, $[\alpha]_D = -89.2°$;

5Z,13E,16Z-9-oxo-11α-15R-dihydroxy-16-fluoro-18,19,20-trinor-17-phenyl-prosta-5,13,16-trienoic acid, $[\alpha]_D = -93°$;

5Z,13E,16Z-9-oxo-11α-15R-dihydroxy-16-fluoro-18,19,20-trinor-17-(2'-furyl)-prosta-15,13,16-trienoic acid, $[\alpha]_D = -79°$; 5Z,13E,16Z-9-oxo-11α-15R-dihydroxy-16-fluoro-18,19,20-trinor-17-(2'-thienyl)-prosta-5,13,16-trienoic acid, $[\alpha]_D = -81°$;

5Z,13E,16Z-9-oxo-11α-15R-dihydroxy-16-fluoro-18,19,20-trinor-17-(2'-pyrrolyl)-prosta-5,13,16-trienoic acid, $[\alpha]_D = -27.5°$;

5Z,13E,16Z-9-oxo-11α-15R-dihydroxy-16-fluoro-18,19,20-trinor-17-(3'-pyridyl)-prosta-5,1,3,16-trienoic acid, $[\alpha]_D = -37.4°$;

5Z,13E,16Z-9-oxo-11α-15R-dihydroxy-16-fluoro-18,19,20-trinor-17-(2'-pyrazinyl)-prosta-5,13,16-trienoic acid, $[\alpha]_D = -41.1°$ 5Z,13E,16Z-9-oxo-11α-15R-dihydroxy-16-fluoro-18,19,20-trinor-17-(3'-isoxazolyl)-prosta-5,13,16-trienoic acid, $[\alpha]_D = -51.3°$;

5Z,13E,16Z-9-oxo-15R-hydroxy-16-fluoro-prosta-5,13,16-trienoic acid, $[\alpha]_D = -42.4°$;

5Z,13E,16Z-9-oxo-15R-hydroxy-16-fluoro-18,19,20-trinor-17-phenyl-prosta-5,13,16-trienoic acid, $[\alpha]_D = -82.7°$;

5Z,13E,16Z-9-oxo-15S-hydroxy-16-fluoro-18,19,20-trinor-17-phenyl-prosta-5,13,16-trienoic acid, $[\alpha]_D = -41°$;

5Z,13E,16Z-9-oxo-15R-hydroxy-16-fluoro-18,19,20-trinor-17-(2'-pyridyl)-prosta-5,13,16-trienoic acid, $[\alpha]_D = -80.5°$;

5Z,13E,16Z-9-oxo-15S-hydroxy-16-fluoro-18,19,20-trinor-17-(2'-pyridyl)-prosta-5,13,16-trienoic acid, $[\alpha]_D = -44.5°$.

EXAMPLE 23

To 0.751 g of 5Z,13E,16Z-9α,11α-15R-trihydroxy-16-fluoro-18,19,20-trinor-17-(2'-furyl)-prosta-5,13,16-trienoic acid methyl ester-9,15-bis-dimethyl-tert-butyl-silyl ether-11-benzoate dissolved in 7 ml of dry methanol, 0.166 g of $K_2CO_3$ were added and the mixture was stirred for 6 hours. The reaction was quenched with iced $NaH_2PO_4$ (70 ml) and was extracted with ethyl acetate; the organic phase was washed with water, dried and the solvent was removed in vacuum. The crude residue was chromatographed on silica gel, using ethyl acetate: n-hexane (20:80) as eluant to give 0.453 g of pure 5Z,13E,16Z-9α,11α-15R-trihydroxy-16-fluoro-18,19,20-trinor-17-(2'-furyl)-prosta-5,13,16-trienoic acid methyl ester-9,15-bis-dimethyl-tert-butyl-silyl ether. This derivative was dissolved in 3 ml of $CH_2Cl_2$ and a slurry of pyridinium chloro cromate (0.266 g) in 5 ml of $CH_2Cl_2$ was added. The mixture was stirred for 1 hour and then 40 ml of diethyl ether were added; the black solid was filtered and the organic phase was distilled yielding a crude residue of 0.383 g of 5Z,13E,16Z-9α-15R-dihydroxy-11-oxo-16-fluoro-18,19,20-trinor-17-(2'-furyl)-prosta-5,13,16-trienoic acid methyl ester-9,15-bis-dimethyl-tert-butylsilyl ether.

The crude 11-oxo-derivative was dissolved in 3 ml of 30% mixture of acetonitrile and 40% aqueous solution of hydrogen fluoride and the solution was stirred for 2.5 hours. Then 50 ml of $CHCl_3$ and 10 ml of water were added and the organic phase was separated, washed, dried and the solvent was removed in vacuum.

The crude was purified by flash chromatography on silica gel using ethyl acetate:n-hexane (70:30) as eluant so obtaining 0.173 g of pure 5Z,13E,16Z-9α-15R-dihydroxy-11-oxo-16-fluoro-18,19,20-trinor-17-(2'-furyl)-prosta-5,13,16-trienoic acid methyl ester, mp. 98° C.

EXAMPLE 24

A solution of 0.470 g of 5Z,13E,16Z-9α,11α-15R-trihydroxy-16-fluoro-18,19,20-trinor-17-phenyl-prosta-5,13,16-trienoic acid methyl ester-15-THP ether in 25 ml of acetone was cooled to −30° C. and then treated with 1.2 ml of Jones' reagent, added over 4 minutes. The reaction mixture was stirred at −30° C. for 15 minutes then was allowed to warm up to −10° and kept 15 minutes at that temperature.

The mixture was left to rise to the room temperature then was diluted with benzene (100 ml) and the organic phase was washed with saturated $(NH_4)_2SO_4$ solution, until neutral, dried and evaporated to dryness yielding 0.450 g of a mixture of 5Z,13E,16Z-9α-15R-dihydroxy-11-oxo-16-fluoro-18,19,20-trinor-17-phenyl-prosta-5,13,16-trienoic acid methyl ester-15-THP-ether and 5Z,13E,16Z-16-fluoro-9-oxo-11α-15R-dihydroxy-18,19,20-trinor-17-phenyl-prosta-5,13,16-trienoic acid methyl ester-15-THP-ether.

The solution of the crude mixture in 25 ml of acetone was treated with an aqueous 20% solution of acetic acid at 40° C. (25 ml) for 2 hours. The solution was extracted with diethyl ether, washed until neutral, dried, and the two compounds were separated by chromatography on silica gel using ethyl acetate:n-hexane (70:30) as eluant to give 0.136 g of pure 5Z,13E,16Z-9α-15R-dihydroxy-11-oxo-16-fluoro-18,19,20-trinor-17-phenyl-prosta-5,13,16-trienoic acid methyl ester (mp. 72° C.) and 0.121 g of pure 5Z,13E,16Z-9-oxo-11α-15R-dihydroxy-16-fluoro-18,19,20-trinor-17-phenyl-prosta-5,13,16-trienoic acid methyl ester (mp. 45° C.).

By analogous procedure the following compounds were obtained:

5Z,13E,16Z-9α-15R-dihydroxy-11-oxo-16-fluoro-prosta,5,13,16-trienoic acid methyl ester;

5Z,16Z-9α-15R-dihydroxy-11-oxo-16-fluoro-prosta-5,16-dien-13-ynoic acid methyl ester;

5Z,13E,16Z-9α-15R-dihydroxy-11-oxo-16-fluoro-18,19,20-trinor-17-cyclohexyl-prosta,5,13,16-trienoic acid methyl ester;

5Z,16Z-9α-15R-dihydroxy-11-oxo-16-fluoro-18,19,20-trinor-17-cyclohexyl-prosta-5,16-dien-13-ynoic acid methyl ester;

5Z,16Z-9α-15R-dihydroxy-11-oxo-16-fluoro-18,19,20-trinor-17-phenyl-prosta-5,16-dien-13-ynoic acid methyl ester;

5Z,13E,16Z-9α,15R-dihydroxy-11-oxo-16-fluoro-18,19,20-trinor-17-(2'-furyl)-prosta-5,13,16-trienoic acid methyl ester;

5Z,16Z-9α-15R-dihydroxy-11-oxo-16-fluoro-18,19,20-trinor-17-(2'-furyl)-prosta-5,16-dien-13-ynoic acid methyl ester;

5Z,13E,16Z-9α-15R-dihydroxy-11-oxo-16-fluoro-18,19,20-trinor-17-(2'-thienyl)-prosta-5,13,16-trienoic acid methyl ester;

5Z,16Z-9α-15R-trihydroxy-11-oxo-16-fluoro-18,19,20-trinor-17-(2'-thienyl)-prosta-5,16-dien-13-ynoic acid methyl ester; as well as 5Z,13E,16Z-9α-15R-dihydroxy-11-oxo-16-fluoro-prosta-5,13,16-trienoic acid;

5Z,16Z-9α-15R-dihydroxy-11-oxo-16-fluoro-prosta-5,16-dien-13-ynoic acid;

5Z,13E,16Z-9α-15R-dihydroxy-11-oxo-16-fluoro-18,19,20-trinor-17-cyclohexyl-prosta-5,13,16-trienoic acid;

5Z,16Z-9α-15R-dihydroxy-11-oxo-16-fluoro-18,19,20-trinor-17-cyclohexyl-prosta-5,16-dien-13-ynoic acid;

5Z,13E,16Z-9α-15R-dihydroxy-11-oxo-16-fluoro-18,19,20-trinor-17-phenyl-prosta-5,13,16-trienoic acid;

5Z,16Z-9α-15R-dihydroxy-11-oxo-16-fluoro-18,19,20-trinor-17-phenyl-prosta-5,16-dien-13-ynoic acid;

5Z,13E,16Z-9α-15R-dihydroxy-11-oxo-16-fluoro-18,19,20-trinor-17-(2'-furyl)-prosta-5,13,16-trienoic acid;

5Z,16Z-9α-15R-dihydroxy-11-oxo-16-fluoro-18,19,20-trinor-17-(2'-furyl)-prosta-5,16-dien-13-ynoic acid;

5Z,13E,16Z-9α-15R-dihydroxy-11-oxo-16-fluoro-18,19,20-trinor-17-(2'-thienyl)-prosta-5,13,16-trienoic acid; and 5Z,16Z-9α-15R-dihydroxy-11-oxo-16-fluoro-18,19,20-trinor-17-(2'-thienyl)-prosta-5,16-dien-13-ynoic acid.

EXAMPLE 25

A solution of 0.40 g of 5Z,13E,16Z-9α,11α-15R-trihydroxy-16-fluoro-18,19,20-trinor-17-phenyl-prosta-5,13,16-trienoic acid in 15 ml of diethyl ether was treated with 1.1 ml of 1N solution of diazomethane. The yellow solution was stirred for 15 minutes then was evaporated to dryness yielding 0.42 g of pure 5Z,13E,16Z-9α,11α-15R-trihydroxy-16-fluoro-18,19,20-trinor-17-phenyl-prosta-5,13,16-trienoic acid methyl ester, $[\alpha]_D = -27°$, $[\alpha]_{365} = -146°$ (C=1, ethanol).

According to the above described procedure starting from 5Z,13E,16Z-9α,11α-15S-trihydroxy-18,19,20-trinor-16-fluoro-17-phenyl-prosta-5,13,16-trienoic acid the pure 5Z,13E,16Z-9α,11α-15S-trihydroxy-16-fluoro-18,19,20-trinor-17-phenyl-prosta-5,13,16-trienoic acid methyl ester was obtained, $[\alpha]_D = +28.1°$ (C=1, ethanol).

By analogous procedure the following methyl esters were obtained:

5Z,13E,16Z-9α,11α-15R-trihydroxy-16-fluoro-prosta-5,13,16-trienoic acid methyl ester, $[\alpha]_D = -21°$;

5Z,16Z-9α,11α-15R-trihydroxy-16-fluoro-prosta-5,16-dien-13-ynoic acid methyl ester, $[\alpha]_D = -21.5°$;

5Z,13E,16Z-9α,11α-15R-trihydroxy-16-fluoro-18,19,20-trinor-17-cyclohexyl-prosta-5,13,16-trienoic acid methyl ester, $[\alpha]_D = -19°$;

5Z,16Z-9α,11α-15R-trihydroxy-16-fluoro-18,19,20-trinor-17-cyclohexyl-prosta-5,16-dien-13-ynoic acid methyl ester, $[\alpha]_D = -17.6°$;

5Z,16Z-9α,11α-15R-trihydroxy-16-fluoro-18,19,20-trinor-17-phenyl-prosta-5,16-dien-13-ynoic acid methyl ester, $[\alpha]_D = -14.7°$;

5Z,13E,16Z-9α,11α-15R-trihydroxy-16-fluoro-18,19,20-trinor-17-(2'-furyl)-prosta-5,13,16-trienoic acid methyl ester, $[\alpha]_D = -21°$; 5Z,13E,16Z-9α,11α-15R-trihydroxy-16-fluoro-18,19,20-trinor-17-(2'-furyl)-prosta-5,16-dien-13-ynoic acid methyl ester, $[\alpha]_D = -38°$;

5Z,13E,16Z-9α,11α-15R-trihydroxy-16-fluoro-18,19,20-trinor-17-(2'-thienyl)-prosta-5,13,16-trienoic acid methyl ester, $[\alpha]_D = -32°$;

5Z,16Z-9α,11α-15R-trihydroxy-16-fluoro-18,19,20-trinor-17-(2'-thienyl)-prosta-5,16-dien-13-ynoic acid methyl ester, $[\alpha]_D = -19.2°$;

5Z,13E,16Z-9-oxo-11α,15R-dihydroxy-16-fluoro-prosta-5,13,16-trienoic acid methyl ester, $[\alpha]_D = -80.5°$;

5Z,13E,16Z-9-oxo-11α,15R-dihydroxy-16-fluoro-20-methyl-prosta-5,13,16-trienoic acid methyl ester, $[\alpha]_D = -72°$;

5Z,13E,16Z-9-oxo-11α,15R-dihydroxy-16-fluoro-20ethyl-prosta-5,13,16-trienoic acid methyl ester, $[\alpha]_D = -70.5°$;

5Z,13E,16Z-9-oxo-11α,15R-dihydroxy-16-fluoro-18,19,20-trinor-17-phenyl-prosta-5,13,16-trienoic acid methyl ester, $[\alpha]_D = -93.3°$;

5Z,13E,16Z-9-oxo-11α,15R-dihydroxy-16-fluoro-18,19,20-trinor-17-(2'-furyl)-prosta-5,13,16-trienoic acid methyl ester, $[\alpha]_D = -81°$;

5Z,13E,16Z-9-oxo-11α,15R-dihydroxy-16-fluoro-18,19,20-trinor-17-(2'-thienyl)-prosta-5,13,16-trienoic acid methyl ester, $[\alpha]_D = -82.5°$; and 5Z,13E,16Z-9-oxo-11α,15R-dihydroxy-16-fluoro-18,19,20-trinor-17-(3'-pyridyl)-prosta-5,13,16-trienoic acid methyl ester, $[\alpha]_D = -38°$.

EXAMPLE 29

CuCl (0.017 g) was added to a solution of 1.373 g of dicyclohexylcarbodiimide (DCC) in 0.661 g of 2-ethoxy-ethanol cooled to 0° C.

The mixture was stirred for about 1 hour at 0° C. then it was allowed to rise to the room temperature and kept at this temperature for 24 hours. The mixture was then diluted with n-hexane (5ml), filtered in silica gel and washed with n-hexane. The solvent was removed to obtain 1.00 g of pure dicyclohexyl-2-ethoxy-ethyl isourea; this product was dissolved in 10 ml of THF and added to a solution of 5Z,13E,16Z-9α,11α-15R-trihydroxy-16-fluoro-18,19,20-trinor-17-phenyl-prosta-5,13,16-trienoic acid (1 g) in 10 ml of dry THF. The mixture was warmed to 60° C. and kept at this temperature for 6 hours. The solvent was removed under vacuum and the crude product thus obtained was purified on silica gel by using a mixture of ethyl acetate: n-hexane (70:30) as eluant. Pure 5Z,13E,16Z-9α,11α-15R-trihydroxy-16-fluoro-18,19,20-trinor-17-phenyl-prosta-5,13,16-trienoic acid 2-ethoxy-ethyl ester (0.925 g) was collected, $[\alpha]_D = -21.4°$ (C=1, CHCl$_3$).

By analogous procedure the following 2-ethoxy-ethyl esters were obtained:

5Z,13E,16Z-9α,11α-15R-trihydroxy-16-fluoro-prosta-5,13,16-trienoic acid 2-ethoxy-ethyl ester, $[\alpha]_D = -16.5°$;

5Z,16Z-9α,11α-15R-trihydroxy-16-fluoro-prosta-5,16-dien-13-ynoic acid 2-ethoxy-ethyl ester, $[\alpha]_D = -18°$;

5Z,13E,16Z-9α,11α-15R-trihydroxy-16-fluoro-18,19,20-trinor-17-cyclohexyl-prosta-5,13,16-trienoic acid 2-ethoxy-ethyl ester, $[\alpha]_D = -15°$;

5Z,16Z-9α,11α-15R-trihydroxy-16-fluoro-18,19,20-trinor-17-cyclohexyl-prosta-5,16-dien-13-ynoic acid 2-ethoxy-ethyl ester, $[\alpha]_D = -16.8°$;

5Z,16Z-9α,11α-15R-trihydroxy-16-fluoro-18,19,20-trinor-17-phenyl-prosta-5,16-dien-13-ynoic acid 2-ethoxy-ethyl ester, $[\alpha]_D = -20°$;

5Z,13E,16Z-9α,11α-15R-trihydroxy-16-fluoro-18,19,20-trinor-17-(2'-furyl)-prosta-5,13,16-trienoic acid 2-ethoxy-ethyl ester, $[\alpha]_D = -19.5°$;

5Z,16Z-9α,11α-15R-trihydroxy-16-fluoro-18,19,20-trinor-17-(2'-furyl)-prosta-5,16-dien-13-ynoic acid 2-ethoxy-ethyl ester, $[\alpha]_D = -30.7°$;

5Z,13E,16Z-9α,11α-15R-trihydroxy-16-fluoro-18,19,20-trinor-17-(2'-thienyl)-prosta-5,13,16-trienoic acid 2-ethoxy-ethyl ester, $[\alpha]_D = -25°$;

5Z,16Z-9α,11α-15R-trihydroxy-16-fluoro-18,19,20-trinor-17-(2'-thienyl)-prosta-5,16-dien-13-ynoic acid 2-ethoxy-ethyl ester, $[\alpha]_D = -20.7°$.

EXAMPLE 27

A solution of potassium tert-butoxide (2.325 g) in dry DMSO (15 ml) under dry argon atmosphere was stirred and, cooling with water bath, [4(methanesulfonylaminocarbonyl)-butyl]triphenylphosphonium bromide (4.35 g) was added to the solution. The temperature of the reacting mixture was kept below 30° C. and the addition was completed in about 15 minutes; then a solution of 1α-{2β-[3'(R)-hydroxy-4'-fluoro-5'-furyl-1'(E),4'(Z)-pentadienyl]-3α,5α-dihydroxy-3,3'-bis-tetrahydropyranyl ether]-cyclopent-1α-yl}-acetaldehyde-γ-hemiacetal (1.7 g) in dry DMSO (15 ml) was added to the obtained mixture.

The reaction was completed in about 1 hour, then the mixture was quenched with water and extracted with diethyl ether. The solvent was removed, the crude product purified by chromatography on silica gel using ethylacetate: n-hexane (1:1) as eluant to give 1.95 g of pure 5Z,13E,16Z-9α,11α-15R-trihydroxy-16-fluoro-18,19,20-trinor-17-(2'-furyl)-prosta-5,13,16-trienoic acid-N-methanesulfonylamide-11,15-bis-tetrahydropyranyl ether.

Deprotecting the obtained product (0.5 g) according to the procedure above described in Example 21, 0.3 g of pure 5Z,13E,16Z-9α,11α-15R-trihydroxy-16-fluoro-18,19,20-trinor-17-(2'-furyl)-prosta-5,13,16-trienoic acid-N-methanesulfonylamide, $[\alpha]_D = -16.5°$ (C=1, CHCl$_3$), were obtained.

Following the procedure above described the following N-methanesulfonylamide derivatives were prepared:

5Z,13E,16Z-9α,11α-15R-trihydroxy-16-fluoro-18,19,20-trinor-17-(3'-isoxazolyl)-prosta-5,13,16-trienoic acid N-methanesulfonylamide, $[\alpha]_D = -16°$;

5Z,16Z-9α,11α-15R-trihydroxy-16-fluoro-18,19,20-trinor-17-(3'-isoxazolyl)-prosta-5,16-dien-13-ynoic acid N-methanesulfonylamide, $[\alpha]_D = -17.5°$;

5Z,13E,16Z-9α,11α-15R-trihydroxy-16-fluoro-prosta-5,13,16-trienoic acid N-methanesulfonylamide, $[\alpha]_D = -20°$;

5Z,16Z-9α,11α-15R-trihydroxy-16-fluoro-prosta-5,16-dien-13-ynoic acid N-methanesulfonylamide, $[\alpha]_D = -19°$;

5Z,13E,16Z-9α,11α-15R-trihydroxy-16-fluoro-20-methylprosta-5,13,16-trienoic acid N-methanesulfonylamide, $[\alpha]_D = -22°$;

5Z,16Z-9α,11α-15R-trihydroxy-16-fluoro-20-methyl-prosta-5,16-dien-13-ynoic acid N-methanesulfonylamide, $[\alpha]_D = -18.5°$;

5Z,13E,16Z-9α,11α-15R-trihydroxy-16-fluoro-20-ethyl-prosta-5,13,16-trienoic acid N-methanesulfonylamide, $[\alpha]_D = -21.8°$;

5Z,16Z-9α,11α-15R-trihydroxy-16-fluoro-20-ethyl-prosta-5,16-dien-13-ynoic acid N-methanesulfonylamide, $[\alpha]_D = -22.5°$;

5Z,13E,16Z-9α,11α-15R-trihydroxy-16-fluoro-18,19,20-trinor-17-cyclohexyl-prosta-5,13,16-trienoic acid N-methanesulfonylamide, $[\alpha]_D = -17.5°$;

5Z,16Z-9α,11α-15R-trihydroxy-16-fluoro-18,19,20-trinor-17-cyclohexyl-prosta-5,16-dien-13-ynoic acid N-methanesulfonylamide, $[\alpha]_D = -15.6°$;

5Z,13E,16Z-9α,11α-15R-trihydroxy-16-fluoro-18,19,20-trinor-17-(3'-chloro-phenyl)-prosta-5,13,16-trienoic acid N-methanesulfonylamide, $[\alpha]_D = -23.7°$;

5Z,13E,16Z-9α,11α-15R-trihydroxy-16-fluoro-18,19,20-trinor-17-(4'-trifluoromethylphenyl)-prosta-5,13,16-trienoic acid N-methanesulfonylamide, $[\alpha]_D = -22.9°$;

5Z,13E,16Z-9α,11α-15R-trihydroxy-16-fluoro-18,19,20-trinor-17-phenyl-prosta-5,13,16-trienoic acid N-methanesulfonylamide, $[\alpha]_D = -24°$;

5Z,16Z-9α,11α-15R-trihydroxy-16-fluoro-18,19,20-trinor-17-phenyl-prosta-5,16-dien-13-ynoic acid N-methanesulfonylamide, $[\alpha]_D = -20.7°$;

5Z,13E,16Z-9α,11α-15R-trihydroxy-16-fluoro-18,19,20-trinor-17-(3'-furyl)-prosta-5,13,16-trienoic acid N-methanesulfonylamide, $[\alpha]_D = -17°$;

5Z,16Z-9α,11α-15R-trihydroxy-16-fluoro-18,19,20-trinor-17-(3'-furyl)-prosta-5,16-dien-13-ynoic acid N-methanesulfonylamide, $[\alpha]_D = -20°$;

5Z,13E,16Z-9α,11α-15R-trihydroxy-16-fluoro-18,19,20-trinor-17-(2'-thienyl)-prosta-5,13,16-trienoic acid N-methanesulfonylamide, $[\alpha]_D = -27°$;

5Z,16Z-9α,11α-15R-trihydroxy-16-fluoro-18,19,20-trinor-17-(2'-thienyl)-prosta-5,16-dien-13-ynoic acid N-methanesulfonylamide, $[\alpha]_D = -25°$;

5Z,13E,16Z-9α,11α-15R-trihydroxy-16-fluoro-18,19,20-trinor-17-(2'-pyrrolyl)-prosta-5,13,16-trienoic acid N-methanesulfonylamide, $[\alpha]_D = -18.5°$;

5Z,16Z-9α,11α-15R-trihydroxy-16-fluoro-18,19,20-trinor-17-(2'-pyrrolyl)-prosta-5,16-dien-13-ynoic acid N-methanesulfonylamide, $[\alpha]_D = -16.5°$;

5Z,13E,16Z-9α,11α-15R-trihydroxy-16-fluoro-18,19,20-trinor-17-(3'-pyridyl)-prosta-5,13,16-trienoic acid N-methanesulfonylamide, $[\alpha]_D = -17°$;

5Z,16Z-9α,11α-15R-trihydroxy-16-fluoro-18,19,20-trinor-17-(3'-pyridyl)-prosta-5,16-dien-13-ynoic acid N-methanesulfonylamide, $[\alpha]_D = -17.2°$;

5Z,13E,16Z-9α,11α-15R-trihydroxy-16-fluoro-18,19,20-trinor-17-(2'-pyrazinyl)-prosta-5,13,16-trienoic acid N-methanesulfonylamide, $[\alpha]_D = -31.7°$;

5Z,16Z-9α,11α-15R-trihydroxy-16-fluoro-18,19,20-trinor-17-(2'-pyrazinyl)-prosta-5,16-dien-13-ynoic acid N-methanesulfonylamide, $[\alpha]_D = -30°$.

In analogous way, using the same procedure and the appropriate triphenylphosphonium derivatives and the suitable bis-THP-ether-lactols, the amides, N,N-dimethyl-amides, N,N-diethyl-amides, piperazin-amides and piperidin-amides were obtained.

EXAMPLE 28

1.5 ml of Jones reagent were dropped into a solution, cooled to −25° C., of 5Z,13E,16Z-9α,11α-15R-trihydroxy-16-fluoro-18,19,20-trinor-17-(2'-furyl)-prosta-5,13,16-trienoic acid-N-methanesulfonylamide-11,15-bis-THP-ether (1.1 g) in acetone (15 ml).

After the addition the temperature was allowed to rise to −8° C. and the reaction mixture was stirred for 20 minutes. The mixture was then diluted with benzene, washed with saturated ammonium sulfate solution until neutral, dried, and the solvent was evaporated at 20° C. under vacuum. The residue (0.85 g) was dissolved in 30 ml of acetone and treated with 1N oxalic acid solution (5.5 ml) for 8 hours at 40° C. After the reaction was completed the acetone was evaporated to give a crude residue which, through chromatography on silica gel using ethyl acetate: n-hexane (35:65) as eluant phase, afforded 0.32 g of pure 5Z,13E,16Z-9-oxo-11α,15R-dihydroxy-16-fluoro-18,19,20-trinor-17-(2'-furyl)-prosta-5,13,16-trienoic acid-N-methanesulfonylamide, $[\alpha]_D = -79°$ (C=1, EtOH).

By proceeding analogously the following compounds were obtained:

5Z,13E,16Z-9-oxo-11α-15R dihydroxy-16-fluoro-prosta-5,13,16,-trienoic acid-N-methanesulfonyl amide, $[\alpha]_D = -81°$;

5Z,16Z-9-oxo-11α-15R dihydroxy-16-fluoro-prosta-5,16-dien-13-ynoic acid-N-methanesulfonyl amide, $[\alpha]_D = -83°$;

5Z,13E,16Z-9-oxo-11α-15R dihydroxy-16-fluoro-20-methylprosta-5,13,16-trienoic acid methanesulfonyl amide, $[\alpha]_D = -69°$;

5Z,13E,16Z-9-oxo-15R-hydroxy-16-fluoro-18,19,20-trinor-17-phenyl-prosta-5,13,16-trienoic acid-N-methanesulfonyl amide, $[\alpha]_D = -49.5°$;

5Z,16Z-9-oxo-11α-15R-dihydroxy-16-fluoro-20-methyl-prosta-5,16-dien-13-ynoic acid-N-methanesulfonyl amide, $[\alpha]_D = -72°$;

5Z,13E,16Z-9-oxo-11α-15R-dihydroxy-16-fluoro-20-ethyl-prosta-5,13,16-dienoic acid-N-methanesulfonyl amide, $[\alpha]_D = -70.5°$;

5Z,16Z-9-oxo-11α-15R-dihydroxy-16-fluoro-20-ethyl-prosta-5,16-dien-13-ynoic acid-N-methanesulfonyl amide, $[\alpha]_D = -71°$;

5Z,13E,16Z-9-oxo-11α-15R-dihydroxy-16-fluoro-18,19,20-trinor-17-(3'-chloro-phenyl)-prosta-5,13,16-trienoic acid-N-methanesulfonyl amide, $[\alpha]_D = -81°$;

5Z,13E,16Z-9-oxo-11α-15R-dihydroxy-16-fluoro-18,19,20-trinor-17-(4'-trifluoromethylphenyl)-prosta-5,13,16-trienoic acid methanesulfonyl amide, $[\alpha]_D = -84°$;

5Z,13E,16Z-9-oxo-11α-15R-dihydroxy-16-fluoro-18,19,20-trinor-17-phenyl-prosta-5,13,16-trienoic acid-N-methanesulfonyl amide, $[\alpha]_D = -91.5°$;

5Z,16Z-9-oxo-11α-15R-dihydroxy-16-fluoro-18,19,20-trinor-17-phenyl-prosta-5,16-dien-13-ynoic acid-N-methanesulfonyl amide, $[\alpha]_D = -90°$.

EXAMPLE 29

A solution of 5Z,13E,16Z-9α,11α-15R-trihydroxy-16-fluoro-18,19,20-trinor-17-phenyl-prosta-5,13,16-trienoic acid methyl ester (0.5 g) in methyl alcohol (10 ml) was cooled with brine and dry NH$_3$ was bubbled into the solution until saturation.

The reaction vessel was closed and the reacting mixture was maintained at room temperature for 24 hours; the NH$_3$ was stripped with nitrogen and methanol was removed. The crude product was purified with preparative chromatographic technique on silica gel using n-hexane:ethyl acetate (1:1) as eluant.

Pure 5Z,13E,16Z-9α,11α-15R-trihydroxy-16-fluoro-18,19,20-trinor-17-phenyl-prosta-5,13,16-trienoic acid amide (0.39 g) was collected, $[\alpha]_D = -24°$ (C=1, EtOH).

Following the same procedure the following amides were obtained:

5Z,16Z-9α,11α-15R-trihydroxy-16-fluoro-18,19,20-trinor-17-phenyl-prosta-5,16-dien-13-ynoic acid amide, $[\alpha]_D = -22°$;

5Z,13E,16Z-9α,11α-15R-trihydroxy-16-fluoro-18,19,20-trinor-17-(2'-furyl)-prosta-5,13,16-trienoic acid amide, $[\alpha]_D = -19.6°$;

5Z,16Z-9α,11α-15R-trihydroxy-16-fluoro-18,19,20-trinor-17-(2'-furyl)-prosta-5,16-dien-13-ynoic acid amide, $[\alpha]_D = -21°$;

5Z,13E,16Z-9α,11α-15R-trihydroxy-16-fluoro-18,19,20-trinor-17-(2'-thienyl)-prosta-5,13,16-trienoic acid amide, $[\alpha]_D = -30°$;

5Z,16Z-9α,11α-15R-trihydroxy-16-fluoro-18,19,20-trinor-17-(2'-thienyl)-prosta-5,16-dien-13-ynoic acid amide, $[\alpha]_D = -26.7°$;

5Z,13E,16Z-9α,11α-15R-trihydroxy-16-fluoro-prosta-5,13,16-trienoic acid amide, $[\alpha]_D = -21.5°$;

5Z,16Z-9α,11α-15R-trihydroxy-16-fluoro-prosta-5,16-dien-13-ynoic acid amide, $[\alpha]_D = -19.7°$;

5Z,13E,16Z-9α,11α-15R-trihydroxy-16-fluoro-18,19,20-trinor-17-cyclohexyl-prosta-5,13,16-trienoic acid amide, $[\alpha]_D = -18°$; and 5Z,16Z-9α,11α-15R-trihydroxy-16-fluoro-18,19,20-trinor-17-cyclohexyl-prosta-5,16-dien-13-ynoic acid amide, $[\alpha]_D = -19.6°$.

EXAMPLE 30

A solution of 5Z,13E,16Z-9α,11α-15R-trihydroxy-16-fluoro-18,19,20-trinor-17-phenyl-prosta-5,13,16-trienoic acid (0.60 g) in 5 ml of ethanol was treated with 15 ml of 0.1N NaOH solution.

The alcohol was removed in vacuum and the aqueous solution was lyophilized to give 0.64 g of dry sodium salt of 5Z,13E,16Z-9α,11α-15R-trihydroxy-16-fluoro-18,19,20-trinor-17-phenyl-prosta-5,13,16-trienoic acid as white powder, $[\alpha]_D = -22°$ (C=1, ethanol).

By analogous procedure the sodium salts of the following compounds were prepared:

5Z,13E,16Z-9α,11α-15R-trihydroxy-16-fluoro-prosta-5,13,16-trienoic acid, $[\alpha]_D = -19.5°$;

5Z,13E,16Z-9α,11α-15R-trihydroxy-16-fluoro-20-methyl-prosta-5,13,16-trienoic acid, $[\alpha]_D = -20°$;

5Z,13E,16Z-9α,11α-15R-trihydroxy-16-fluoro-20-ethyl-prosta-5,13,16-trienoic acid, $[\alpha]_D = -20.8°$;

5Z,13E,16Z-9α,11α-15R-trihydroxy-16-fluoro-18,19,20-trinor-17-cyclohexyl-prosta-5,13,16-trienoic acid, $[\alpha]_D = -17.9°$;

5Z,13E,16Z-9α,11α-15R-trihydroxy-16-fluoro-18,19,20-trinor-17-(3'-chloro-phenyl)-prosta-5,13,16-trienoic acid, $[\alpha]_D = -24.5°$;

5Z,13E,16Z-9α,11α-15R-trihydroxy-16-fluoro-18,19,20-trinor-17-(4'-trifluoromethylphenyl)-prosta-5,13,16-trienoic acid, $[\alpha]_D = -23°$;

5Z,13E,16Z-9α,11α-15R-trihydroxy-16-fluoro-18,19,20-trinor-17-(2'-furyl)-prosta-5,13,16-trienoic acid, $[\alpha]_D = -19.5°$;

5Z,13E,16Z-9α,11α-15R-trihydroxy-16-fluoro-18,19,20-trinor-17-(2'-thienyl)-prosta-5,13,16-trienoic acid, $[\alpha]_D = -18.8°$;

5Z,13E,16Z-9α,11α-15R-trihydroxy-16-fluoro-18,19,20-trinor-17-(2'-pyrrolyl)-prosta-5,13,16-trienoic acid, $[\alpha]_D = -15°$;

5Z,13E,16Z-9α,11α-15R-trihydroxy-16-fluoro-18,19,20-trinor-17-(3'-pyridyl)-prosta-5,13,16-trienoic acid, $[\alpha]_D = -15.5°$;

5Z,13E,16Z-9α,11α-15R-trihydroxy-16-fluoro-18,19,20-trinor-17-(2'-pyrazinyl)-prosta-5,13,16-trienoic acid, $[\alpha]_D = -33°$; and 5Z,13E,16Z-9α,11α-15R-trihydroxy-16-fluoro-18,19,20-trinor-17-(3'-isoxazolyl)-prosta-5,13,16-trienoic acid, $[\alpha]_D = -17°$.

FORMULATION EXAMPLES

Formulation I: Tablet (0.5 mg)

Tablets, each weighing 80 mg and containing 0.5 mg of the active substance, are manufactured as follows:

| Composition (for 100,000 tablets) | |
|---|---|
| 5Z,13E,16Z—9-oxo-15R—hydroxy-16-fluoro-18,19,20-trinor-17-phenyl-prosta-5,13,16-trienoic acid methyl ester | 50 g |
| Lactose | 5000 g |
| Corn starch | 2770 g |
| Talc powder | 150 g |
| Magnesium stearate | 30 g |

5Z,13E,16Z-9-oxo-15R-hydroxy-16-fluoro-18,19,20-trinor-17-phenyl-prosta-5,13,16-trienoic acid methyl ester, the lactose and half the corn starch are mixed; the mixture is then forced through a sieve of 0.5 mm mesh size. Corn starch (18 g) is suspended in warm water (180 ml). The resulting paste is used to granulate the powder. The granules are dried, comminuted on a sieve of mesh size 1.4 mm, then the remaining quantity of starch, talc and magnesium stearate is added, carefully mixed and processed into tablets using punches of 5 mm diameter.

Formulation II: Intramuscular Injection (0.5 mg/ml)

An injectable pharmaceutical composition was manufactured by dissolving 0.5 mg of 5Z,13E,16Z-9-oxo-15R-hydroxy-16-fluoro-18,19,20-trinor-17-phenyl-prosta-5,13,16-trienoic acid methyl ester in sterile propyleneglycol (1 ml) and ampoules of 1 ml were sealed.

Following the same procedure ampoules of 1–5 ml of 5Z,13E,16Z-9α,11α,15R-trihydroxy-16-fluoro- 18,19,20-trinor-17-phenyl-prosta-5,13,16-trienoic acid methyl ester in sterile propyleneglycol were prepared containing 0.5 mg/ml of active product.

Formulation III: Capsule (0.5 mg)

| | |
|---|---|
| 5Z,13E,16Z—9-oxo-11α,15R—dihydroxy-16-fluoro-18,19,20-trinor-17-phenyl-prosta-5,13,16-trienoic acid N—methanesulfonylamide | 5 g |
| Lactose | 903 g |
| Corn starch | 90 g |
| Magnesium stearate | 2 g |

This formulation was encapsulated in two-piece hard gelatin capsules and dosed at 100 mg for each capsule.

Formulation IV: Suppository Form (0.5 mg)

Vaginal pessaries, each weighing 2.4 g and containing mg 0.5 of the active substance were manufactured as described below:

| Composition (for 10,000 suppositories) | |
|---|---|
| 5Z,13E,16Z—9-oxo-15R—hydroxy-16-fluoro-18,19,20-trinor-17-phenyl-prosta-5,13,16-trienoic acid methyl ester | 5 g |
| Esterinum B ® | 23.995 g |

The glycerid semisynthetic solid "Esterinum B" was melted at 60° C., then stirred and cooled at 40° C. with external thermostatic bath. 5 g of 5Z,13E,16Z-9-oxo-15R-hydroxy-16-fluoro-18,19,20-trinor-17-phenyl-prosta-5,13,16-trienoic acid methyl ester were then added and stirring was continued until homogeneity.

The resulting melted mass was processed into suppository forms each weighing 2.4 g. In analogous way identical pessaries were prepared but containing the compound 5Z,13E,16Z-9-oxo-11α,15R-dihydroxy-16-fluoro-18,19,20-trinor-17-phenyl-prosta-5,13,16-trienoic acid methyl ester as the active principle.

We claim:

1. A compound of the following formula (I)

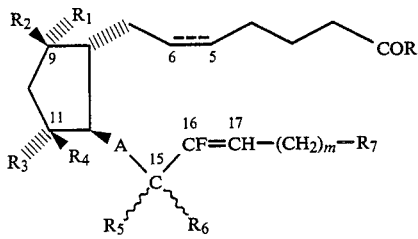

wherein
R is
(1) —OH or —OR', wherein R' is $C_1$–$C_6$ alkyl optionally substituted by phenyl cyclopentyl, cyclohexyl, furyl, tetrahydrofuryl, or pyridyl;
(2)

wherein each of R" and R''' is, independently, hydrogen; $C_1$–$C_6$ alkyl; phenyl; furyl, tetrahydrofuryl, pyridyl; or R" and R''', together with the nitrogen atom to which they are linked, are morpholino, thiomorpholino, piperidino or piperazino;
(3) —W—$(CH_2)_n$—X wherein W is —O— or —NH—, n is an integer of 1 to 4 and X represents a group —OR' or a group

wherein R', R" and R''' are as defined above; or
(4) —$NHSO_2$—$R^{IV}$, wherein $R^{IV}$ is $C_1$–$C_4$ alkyl, phenyl or phenyl substituted by $C_1$–$C_4$ alkyl;
one of $R_1$ and $R_2$ is hydrogen and the other is hydroxy or $R_1$ and $R_2$, taken together, form an oxo group;
one of $R_3$ and $R_4$ is hydrogen and the other is hydroxy or $R_3$ and $R_4$ are both hydrogen or, taken together, form an oxo group;
one of $R_5$ and $R_6$ is hydroxy and the other is hydrogen, $C_1$–$C_6$ alkyl, $C_2$–$C_6$ alkenyl, $C_2$–$C_6$ alkynyl, or phenyl;
m is zero or an integer of 1 to 3;
$R_7$ is unsubstituted phenyl or phenyl substituted by one or more substituents chosen from $C_1$–$C_4$ alkyl, $C_1$–$C_4$-alkoxy, tri-halo-$C_1$–$C_4$-alkyl, halogen,

wherein each of $R^V$ and $R^{VI}$ is, independently, hydrogen, $C_1$–$C_4$-alkyl or phenyl;
A is trans —CH=CH—, —$CH_2$—$CH_2$— or —C≡C—, and the symbol ---- represents a single bond or a cis double bond, with the condition that $R_3$ and $R_4$ do not form an oxo group when $R_1$ and $R_2$ form an oxo group,
and the pharmaceutically or veterinarily acceptable salts thereof.

2. A compound of formula (I) according to claim 1, wherein
R is
(1) —OH or —OR' wherein R' is $C_1$–$C_6$ alkyl; or
(2)

wherein each of R" and R''' is, independently, hydrogen or $C_1$–$C_6$ alkyl; or
(3) —W—$(CH_2)_n$—X wherein W is —O—, n is 2 and X is —OR' wherein R' is $C_1$–$C_6$ alkyl;
one of $R_1$ and $R_2$ is hydrogen and the other is hydroxy or $R_1$ and $R_2$, taken together, form an oxo group;
one of $R_3$ and $R_4$ is hydrogen and the other is hydroxy or $R_3$ and $R_4$ are both hydrogen;
one of $R_5$ and $R_6$ is hydrogen and the other is hydroxy;
m is zero;
$R_7$ is unsubstituted phenyl or phenyl substituted by halogen or tri-halo-methyl;
A is —CH=CH-trans or —C≡C—; and the symbol ---- represents a cis-double bond or a single bond,
and the pharmaceutically or veterinarily acceptable salts thereof.

3. A compound of formula (I) according to claim 2, wherein $R_7$ is phenyl, chloro-phenyl, trifluoromethylphenyl.

4. A compound of formula (I) according to claim 1, wherein

R is —OH or —OR' wherein R' is $C_1$-$C_4$ alkyl;

$R_1$ is hydroxy and $R_2$ is hydrogen or $R_1$ and $R_2$, taken together, form an oxo group;

$R_3$ is hydroxy and $R_4$ is hydrogen or $R_3$ and $R_4$ are both hydrogen;

one of $R_5$ and $R_6$ is hydrogen and the other is hydroxy;

m is zero;

$R_7$ is phenyl, optionally substituted by a halogen atom or by a trifluoromethyl group;

A is —CH=CH-trans or —C≡C—; and the symbol ---- represents a cis-double bond or a single bond,
and the pharmaceutically or veterinarily acceptable salts thereof.

5. A compound of formula (I) according to claim 4, wherein A is —CH=CH-trans.

6. A compound selected from the group consisting of:

5Z,13E,16Z-9α,11α,15R-trihydroxy-16-fluoro-18,19,20-trinor-17-phenyl-prosta-5,13,16-trienoic acid and its methyl ester;

5Z,16Z-9α,11α,15R-trihydroxy-16-fluoro-18,19,20-trinor-17-phenyl-prosta-5,16-dien-13-ynoic acid and its methyl ester;

5Z,13E,16Z-9-oxo-11α,15R-dihydroxy-16-fluoro-18,19,20-trinor-17-phenyl-prosta-5,13,16-trienoic acid and its methyl ester;

13E,16Z-9-oxo-11α,15R-dihydroxy-16-fluoro-18,19,20-trinor-17-phenyl-prosta-13,16-dienoic acid and its methyl ester;

5Z,13E,16Z-9-oxo-15S-hydroxy-16-fluoro-18,19,20-trinor-17-phenyl-prosta-5,13,16-trienoic acid and its methyl ester;

13E,16Z-9-oxo-15R-hydroxy-16-fluoro-18,19,20-trinor-17-phenyl-prosta-13,16-dienoic acid and its methyl ester, and the pharmaceutically or veterinarily acceptable salts of the free acids.

7. A process for the preparation of a compound of formula (I) or a salt thereof according to claim 1, the said process comprising:

(1) submitting to reduction or Grignard reaction the $C_{15}$ carbonyl group of a compound of formula (II)

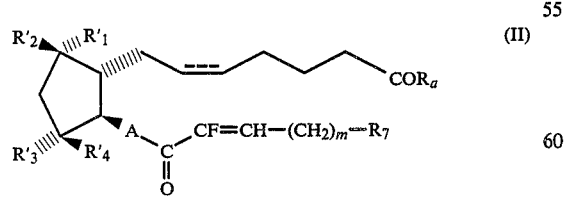

wherein

A, m and $R_7$ are as defined in claim 1;

$R_a$ is R, as defined in claim 23, or a group —OQ wherein Q is a protecting group for the carboxylic function;

one of $R'_1$ and $R'_2$ is hydrogen and the other is a free or protected hydroxy or $R'_1$ and $R'_2$, taken together, form a protected oxo group;

and one of $R'_3$ and $R'_4$ is hydrogen and the other is a free or protected hydroxy or $R'_3$ and $R'_4$ are both hydrogen or $R'_3$ and $R'_4$, taken together, form a protected oxo group, and, in any order, removing the protecting groups possibly present and, if desired, separating the obtained epimeric mixture of the 15S- and 15R-hydroxy compounds into the single epimers; or (2) selectively dehydrohalogenating a compound of formula (III)

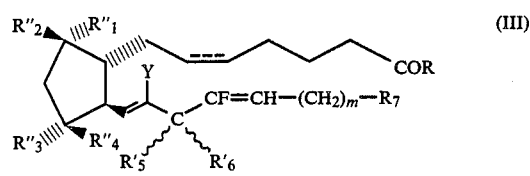

wherein

R, m and $R_7$ are as defined in claim 23, one of $R''_1$ and $R''_2$ is hydrogen and the other is a free or protected hydroxy or $R''_1$ and $R''_2$, taken together, form an oxo group; one of $R''_3$ and $R''_4$ is hydrogen and the other is a free or protected hydroxy or $R''_3$ and $R''_4$ are both hydrogen or, taken together, form an oxo group; one of $R''_5$ and $R''_6$ is a free or protected hydroxy and the other is hydrogen, $C_1$-$C_6$ alkyl, $C_2$-$C_6$ alkenyl, $C_2$-$C_6$ alkynyl or phenyl; and Y is chlorine, bromine or iodine, and removing the protecting groups possibly present, so obtaining a compound of formula (I) wherein A is —C≡C—; or (3) oxidizing a compound of formula (IV)

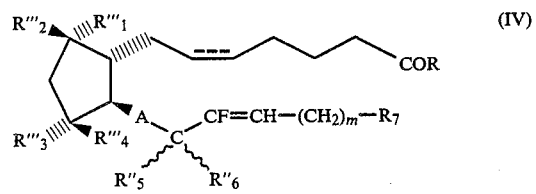

wherein

R, A, m and $R_7$ are as defined in claim 23, at least one of $R'''_1$, $R'''_2$, $R'''_3$ and $R'''_4$ is a free hydroxy group and the others of $R'''_1$, $R'''_2$, $R'''_3$ and $R'''_4$ have, respectively, the meanings reported above for $R''_1$, $R''_2$, $R''_3$ and $R''_4$, except oxo; one of $R''_5$ and $R''_6$ is hydrogen, $C_1$-$C_6$ alkyl, $C_2$-$C_6$-alkenyl, $C_2$-$C_6$ alkynyl or phenyl, and the other is a protected hydroxy, and removing the protecting groups, so obtaining, according to the used starting material, either a compound of formula (I) wherein $R_1$ and $R_2$, taken together, form an oxo group, or a compound of formula (I) wherein $R_3$ and $R_4$, taken together, form an oxo group, or a mixture of said oxidation products and, in this case, separating the obtained mixture into the individual oxidation products; or (4) reacting a compound of formula (V)

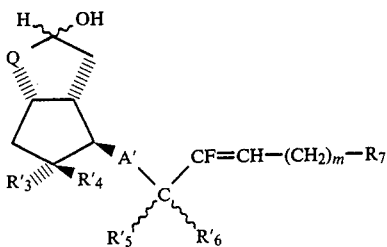

wherein
$R'_3$, $R'_4$, $R'_5$, $R'_6$, m and $R_7$ are as defined above or in claim 1, and A' is trans —CH=CH, —CH$_2$—CH$_2$—, —C≡C— or —CH=CY—
wherein Y is as defined above, with a Wittig reagent comprising a group of formula —(CH$_2$)$_4$—COR wherein R is as defined above, and removing the protecting groups possibly present, so obtaining a compound of formula (I) wherein the symbol ---- represents a cis double bond, $R_1$ is hydroxy and $R_2$ is hydrogen, and, if desired, converting the obtained compound into the corresponding compound of formula (I) wherein $R_1$ is hydrogen and $R_2$ is hydroxy, or into the corresponding compound of formula (I) where $R_1$ and $R_2$, taken together, form an oxo group; and, if desired, converting a compound of formula (I) wherein R is —OH and wherein the hydroxy groups present may be free or protected, or a reactive derivative thereof, into a compound of formula (I)
wherein R is other than —OH through esterification or amidation reactions followed by removal of the protecting groups possibly present, and/or, if desired, salifying a compound of formula (I) or obtaining a free compound of formula (I) from a salt thereof, and/or, if desired, separating a mixture of isomers of formula (I) into the single isomers.

8. A pharmaceutical or veterinary composition containing a compound of formula (I) according to claim 1, 2, 3, 4, 5 or 6 and a pharmaceutically or veterinarily acceptable carrier or diluent.

9. A compound, suitable for use in the preparation of a compound of formula (I) as defined in claim 1, having the formula (II)

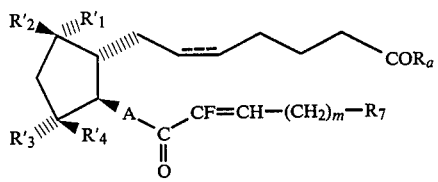

wherein
A, m and $R_7$ are as defined in claim 1;
$R_a$ is R, as defined in claim 2, or a group —OQ wherein Q is a protecting group for the carboxylic function;
one of $R'_1$ and $R'_2$ is hydrogen and the other is a free or protected hydroxy or $R'_1$ and $R'_2$, taken together, form a protected oxo group;
and one of $R'_3$ and $R'_4$ is hydrogen and the other is a free or protected hydroxy or $R'_3$ and $R'_4$ are both hydrogen or $R'_3$ and $R'_4$, taken together, form a protected oxo group.

10. A compound, suitable for use in the preparation of a compound of formula (I) as defined in claim 1, in which A is —C≡C—, having the formula (III)

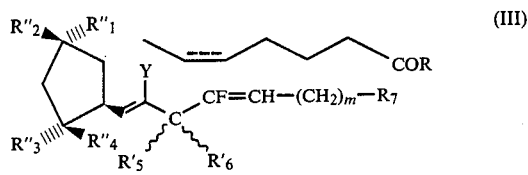

wherein
R, m and $R_7$ are as defined in claim 1, one of $R''_1$ and $R''_2$ is hydrogen and the other is a free or protected hydroxy or $R''_1$ and $R''_2$, taken together, form an oxo group; one of $R''_3$ and $R''_4$ is hydrogen and the other is a free or protected hydroxy or $R''_3$ and $R''_4$ are both hydrogen or, taken together, form an oxo group; one of $R'_5$ and $R'_6$ is a free or protected hydroxy and the other is hydrogen, C$_1$-C$_6$ alkyl, C$_2$-C$_6$ alkenyl, C$_2$-C$_6$ alkynyl or phenyl; and Y is chlorine, bromine or iodine.

11. A compound, suitable for use in the preparation of a compound of formula (I) as defined in claim 1, having the formula (IV)

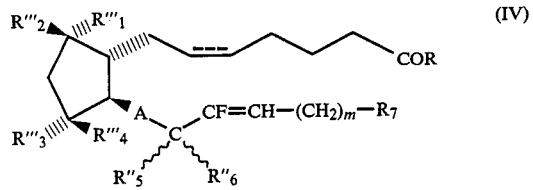

R, A, m and $R_7$ are as defined in claim 23, at least one of $R'''_1$, $R'''_2$, $R'''_3$ and $R'''_4$ is a free hydroxy group and the others of $R'''_1$, $R'''_2$, $R'''_3$ and $R'''_4$ are as defined in claim 32 for, respectively, $R''_1$, $R''_2$, $R''_3$ and $R''_4$ except that they do not represent oxo; one of $R''_5$ and $R''_6$ is hydrogen, C$_1$-C$_6$ alkyl, C$_2$-C$_6$-alkenyl, C$_2$-C$_6$ alkynyl or phenyl, and the other is a protected hydroxy.

12. A compound, suitable for use in the preparation of a compound of formula (I) as defined in claim 1 having the formula (X):

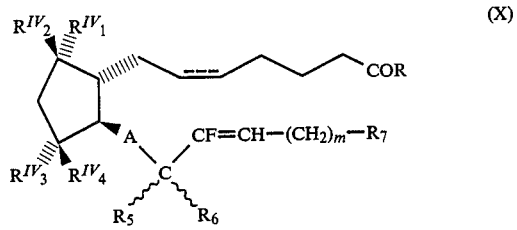

wherein R, A, $R_5$, $R_6$, m and $R_7$ are as defined in claim 1, one of $R^{IV}_1$ and $R^{IV}_2$ is hydrogen and the other is an esterified hydroxy group; and one of $R^{IV}_3$ and $R^{IV}_4$ is hydrogen and the other is an etherified hydroxy or $R^{IV}_3$ and $R^{IV}_4$ are both hydrogen.

13. A compound, suitable for use in the preparation of a compound of formula (I) as defined in claim 1, having the formula (XI)

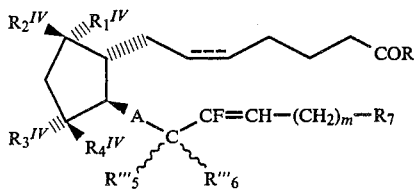 (XI)

wherein R, A, m and $R_7$ are as defined in claim 1, $R^{IV}_1$, $R^{IV}_2$, $R^{IV}_3$ and $R^{IV}_4$ are as defined in claim 12, and one of $R'''_5$ and $R'''_5$ and $R'''_6$ is an etherified hydroxy and the other is hydrogen, $C_1$-$C_6$ alkyl, $C_2$-$C_6$ alkenyl, $C_2$-$C_6$ alkynyl or phenyl.

14. A compound, suitable for use in the preparation of a compound of formula (I) as defined in claim 1, having the formula (XII):

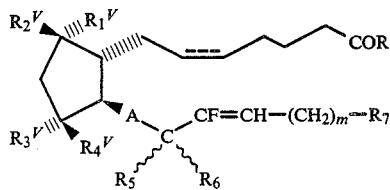 (XII)

wherein R, A, $R_5$, $R_6$, m and $R_7$ are as defined in claim 1, one of $R^V_1$ and $R^V_2$ is hydrogen and the other is an etherified hydroxy; and one of $R^V_3$ and $R^V_4$ is hydrogen and the other is an esterified hydroxy.

15. A compound, suitable for use in the preparation of a compound of formula (I) as defined in claim 1, having the formula (XIII)

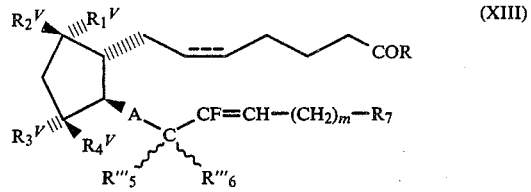 (XIII)

wherein R, A, m and $R_7$ are as defined in claim 1, $R^V_1$, $R^V_2$, $R^V_3$ and $R^V_4$ are as defined in claim 14, and $R'''_5$ and $R'''_6$ are as defined in claim 13.

16. A method of producing a luteolytic effect in a patient in need of it, said method comprising administering an effective amount of a compound of claim 1.

17. A method of producing a luteolytic effect in a patient in need of it, said method comprising administering an effective amount of a pharmaceutical composition of claim 8.

* * * * *

UNITED STATES PATENT AND TRADEMARK OFFICE
CERTIFICATE OF CORRECTION

PATENT NO. : 4,626,597  Page 1 of 2

DATED : December 2, 1986

INVENTOR(S) : Franco FAUSTINI et al

It is certified that error appears in the above-identified patent and that said Letters Patent is hereby corrected as shown below:

Column 2 line 18; column 8 line 20; column 42 line 37; column 43 lines 1 and 22; column 45 line 22, delete the symbol "----" and replace by -- ---- --

Column 6 formula (II) add dotted line to connect group $R'_3$ to the 5-membered ring.

Column 7 line 54 delete "R'''HD$_2$R'''$_3$" and replace by --R'''$_2$R'''$_3$--

Column 7 line 55 delete "R'''$_1$,R'''$_3$" and replace by -- R'''$_1$,R'''$_2$,R'''$_3$ --

Column 11 line 47 delete "-W-(CH$_2$)$_n$-W" and replace by -- -W-(CH$_2$)$_n$-X --

Column 13 line 3 delete "optical" and replace by --optional--

Column 13 line 55 delete "-C≡-," and replace by -- -C≡C- --

Column 43 line 66 delete "claim 23" and replace by --claim 1--

Column 44 lines 25 and 51 delete "claim 23" and replace by --claim 1-- in both instances.

Column 46 formula (III) add dotted lines to connect the alpha chain to the 5-membered ring.

UNITED STATES PATENT AND TRADEMARK OFFICE
CERTIFICATE OF CORRECTION

PATENT NO. : 4,626,597

DATED : December 2, 1986

INVENTOR(S) : Franco FAUSTINI et al

It is certified that error appears in the above-identified patent and that said Letters Patent is hereby corrected as shown below:

Column 46 line 42 delete "claim 32" and replace by --claim 10--

Column 46 line 62 delete "$R_{IV1}$" and replace by -- $R_1^{IV}$ --

Signed and Sealed this

Eleventh Day of August, 1987

Attest:

DONALD J. QUIGG

Attesting Officer

Commissioner of Patents and Trademarks